US010405797B1

(12) United States Patent
Uehara

(10) Patent No.: US 10,405,797 B1
(45) Date of Patent: Sep. 10, 2019

(54) WEARABLE DEVICE AND SYSTEM FOR TEACHING CORE USAGE AND RELATED APPLICATIONS

(71) Applicant: Alert Core, Inc., Kailua, HI (US)

(72) Inventor: Gregory Takeo Uehara, Kailua, HI (US)

(73) Assignee: Alert Core, Inc., Kailua, HI (US)

( * ) Notice: Subject to any disclaimer, the term of this patent is extended or adjusted under 35 U.S.C. 154(b) by 1003 days.

(21) Appl. No.: 14/817,964

(22) Filed: Aug. 4, 2015

Related U.S. Application Data

(63) Continuation-in-part of application No. 14/132,808, filed on Dec. 18, 2013, now Pat. No. 9,226,706, and a continuation-in-part of application No. 14/789,136, filed on Jul. 1, 2015, now Pat. No. 9,706,962, and a
(Continued)

(51) Int. Cl.
*A61B 5/00* (2006.01)
*A61B 5/11* (2006.01)
*A63B 71/06* (2006.01)

(52) U.S. Cl.
CPC .......... *A61B 5/486* (2013.01); *A61B 5/1107* (2013.01); *A61B 5/1123* (2013.01);
(Continued)

(58) Field of Classification Search
CPC ....... A61B 5/486; A61B 5/1123; A61B 5/743; A61B 5/4519; A61B 5/6831; A61B 5/6898; A61B 5/1107; A63B 71/0619
See application file for complete search history.

(56) References Cited

U.S. PATENT DOCUMENTS 3,913,563 A * 10/1975 Ball ..................... A61B 5/4356
356/32
4,320,667 A * 3/1982 Forrester ................ G01L 1/144
361/283.2
(Continued)

FOREIGN PATENT DOCUMENTS

WO WO2009013490 1/2009
WO WO 2009013490 A1 * 1/2009

OTHER PUBLICATIONS

Derdevic, et al., MC Sensor—A Novel Method for Measurement of Muscle Tension, Sensors Journal, Sep. 28, 2011, pp. 9411-9425, Molecular Diversity Preservation International, www.mdpi.com, Basel Switzerland.

*Primary Examiner* — Rene T Towa
(74) *Attorney, Agent, or Firm* — Staniford Tomita LLP

(57) ABSTRACT

The system includes a movement sensor and a core contraction sensor in communication with a processor. The core contraction sensor is placed on the core muscles of a user and transmits core contraction signals to the processor. The processor receives movement signals from the movement sensor and identifies user movements that are qualifying movements that benefit from core contractions. The processor also monitors the timing between the qualifying movements and the core contractions to identify protected and unprotected qualifying movements. The system can also include a memory for storing core scores that are calculated from the protected and unprotected qualifying movements, exercise information and core sensor calibration information. The core contraction information can be used to calibrate the core contraction sensor. The core contraction and movement information can be transmitted to a therapist who can monitor the user's activities and provide instructional feedback.

11 Claims, 22 Drawing Sheets

Related U.S. Application Data continuation-in-part of application No. 14/800,931, filed on Jul. 16, 2015.

(60) Provisional application No. 62/032,664, filed on Aug. 4, 2015, provisional application No. 61/739,160, filed on Dec. 19, 2012, provisional application No. 62/027,409, filed on Jul. 22, 2014, provisional application No. 62/019,522, filed on Jul. 1, 2014, provisional application No. 62/025,929, filed on Jul. 17, 2014.

(52) U.S. Cl.
CPC .......... *A61B 5/4519* (2013.01); *A61B 5/6831* (2013.01); *A61B 5/6898* (2013.01); *A61B 5/743* (2013.01); *A63B 71/0619* (2013.01)

(56) References Cited

U.S. PATENT DOCUMENTS

| | | | | |
|---|---|---|---|---|
| 5,728,027 A | * | 3/1998 | Sinaiko | A63B 23/0244 340/573.1 |
| 5,755,674 A | * | 5/1998 | Watson | A61B 5/0404 600/587 |
| 2003/0187370 A1 | * | 10/2003 | Kodama | A61B 5/033 600/591 |
| 2010/0191154 A1 | * | 7/2010 | Berger | A61B 5/02411 600/595 |
| 2010/0234699 A1 | * | 9/2010 | Lanfermann | A63B 24/0006 600/301 |
| 2012/0116259 A1 | * | 5/2012 | McConnell | A63B 21/153 600/595 |

* cited by examiner

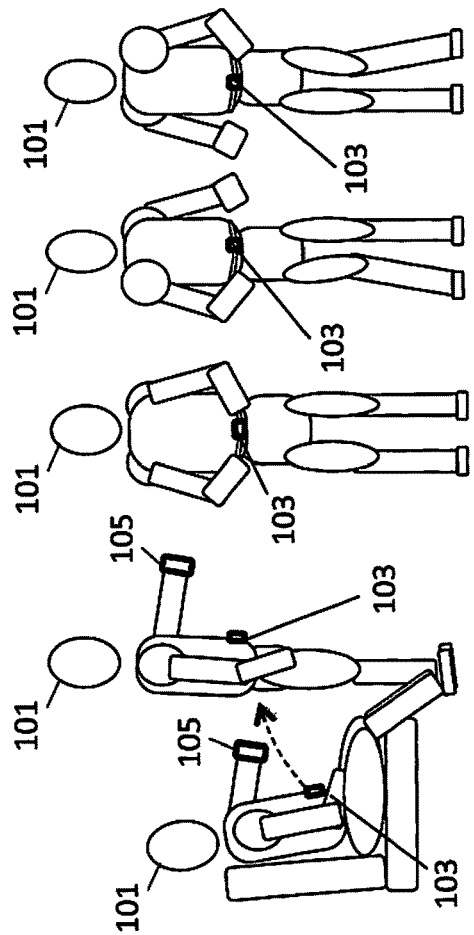
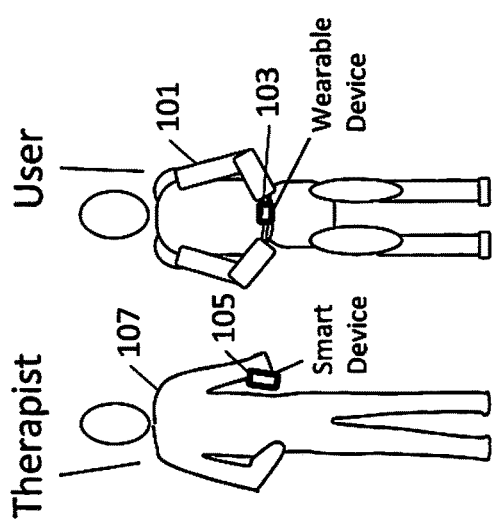
FIG. 1c
FIG. 1b
FIG. 1a

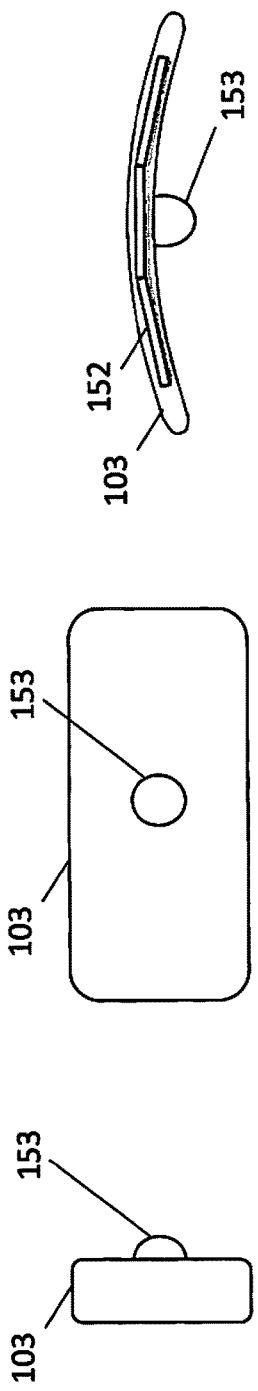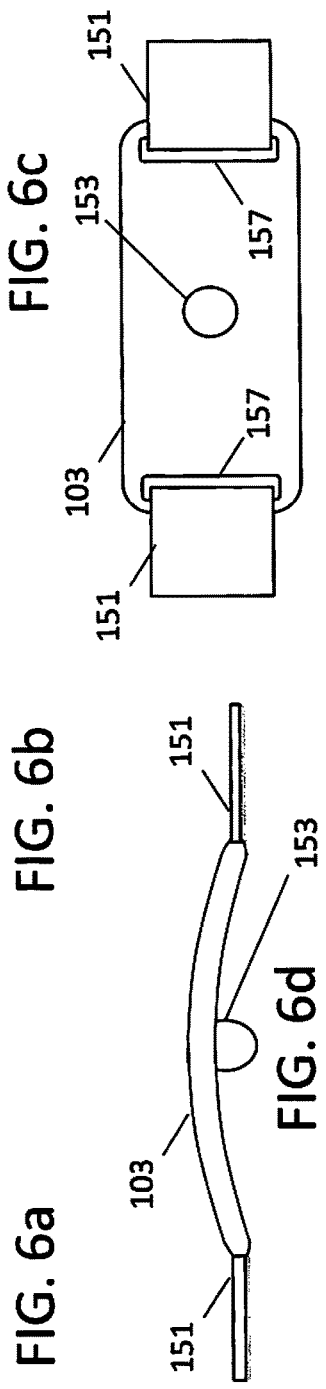

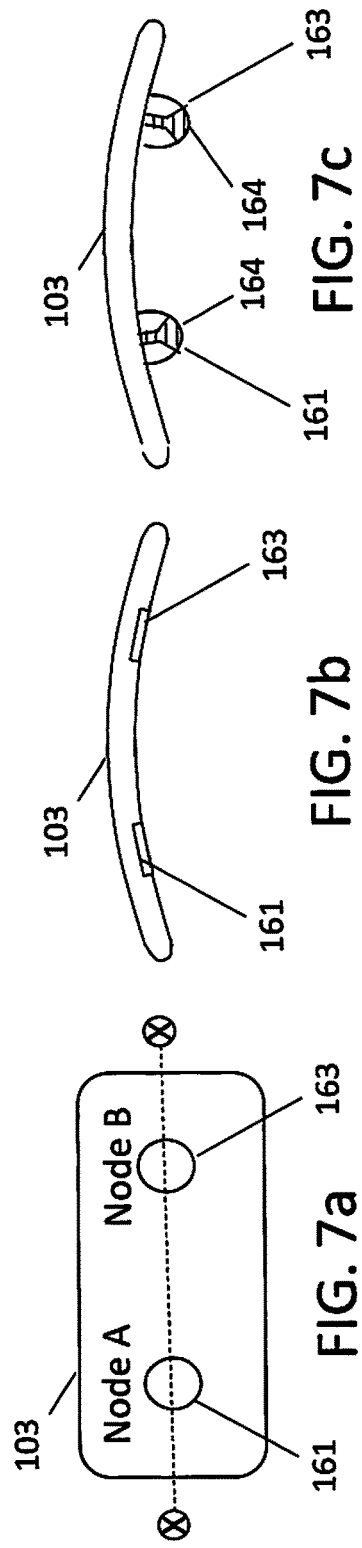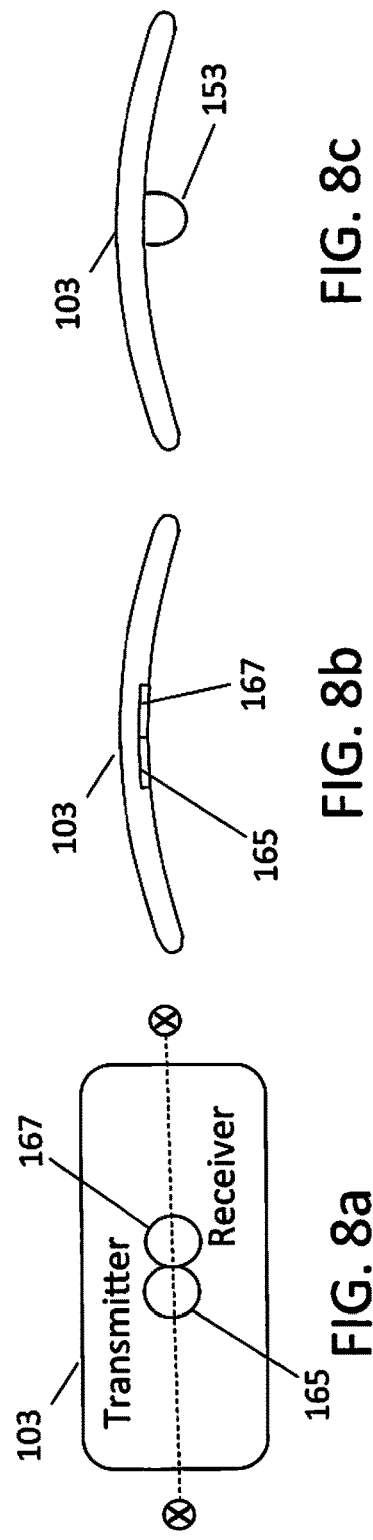

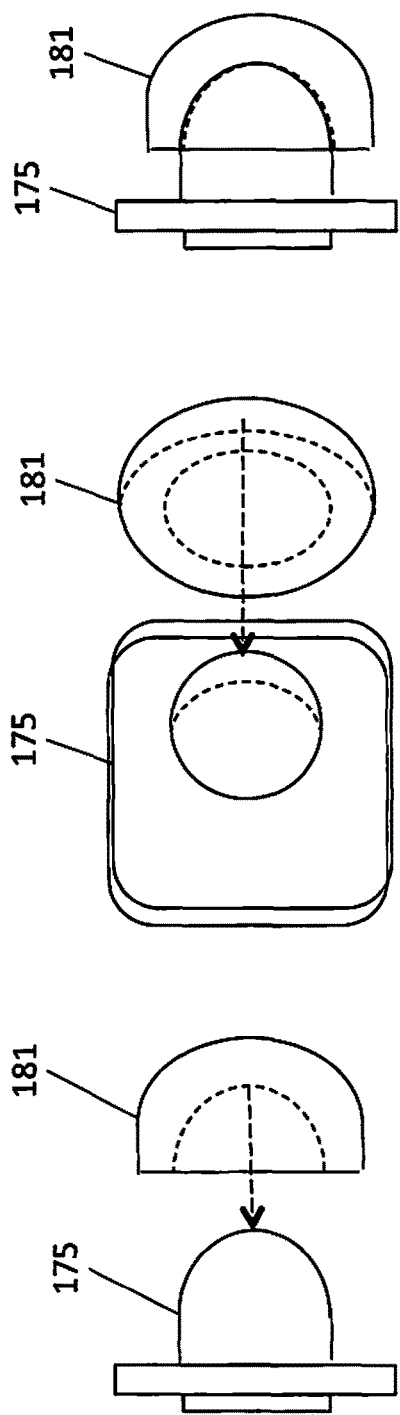

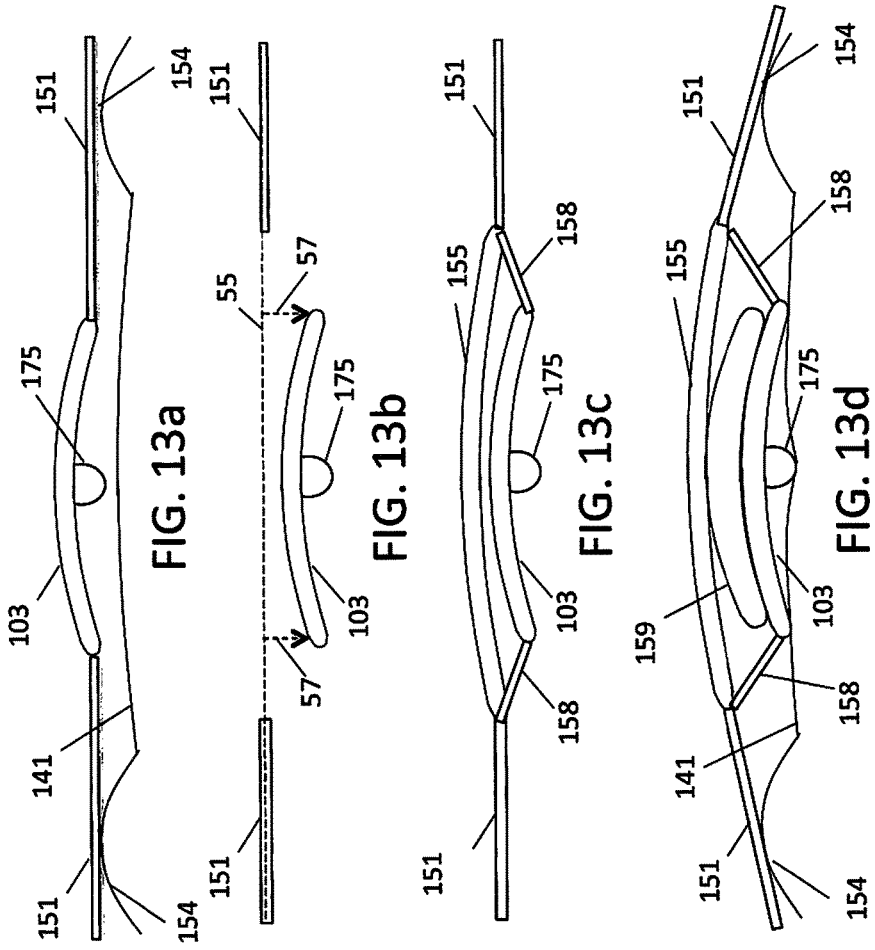

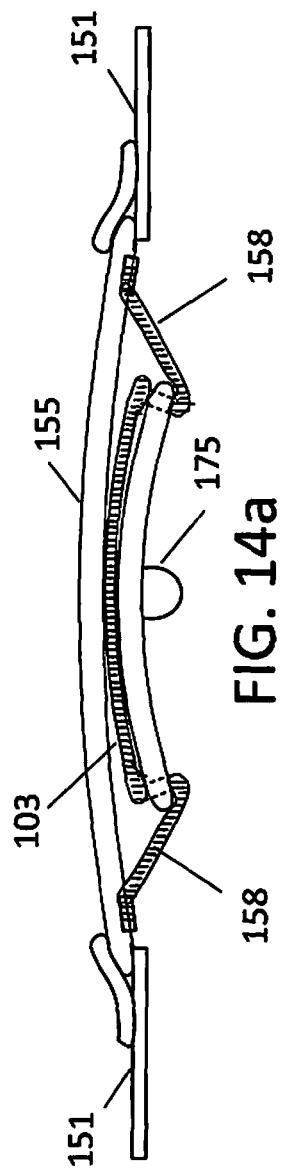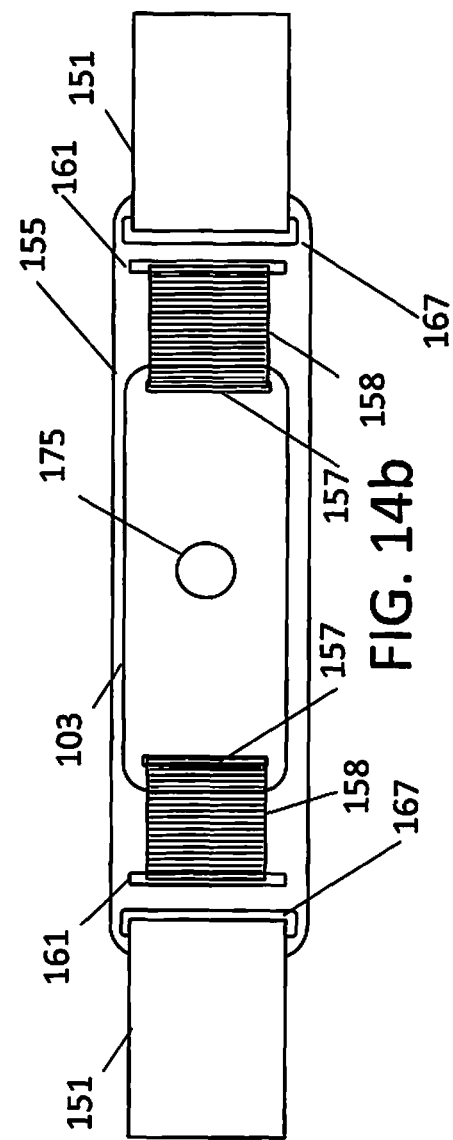

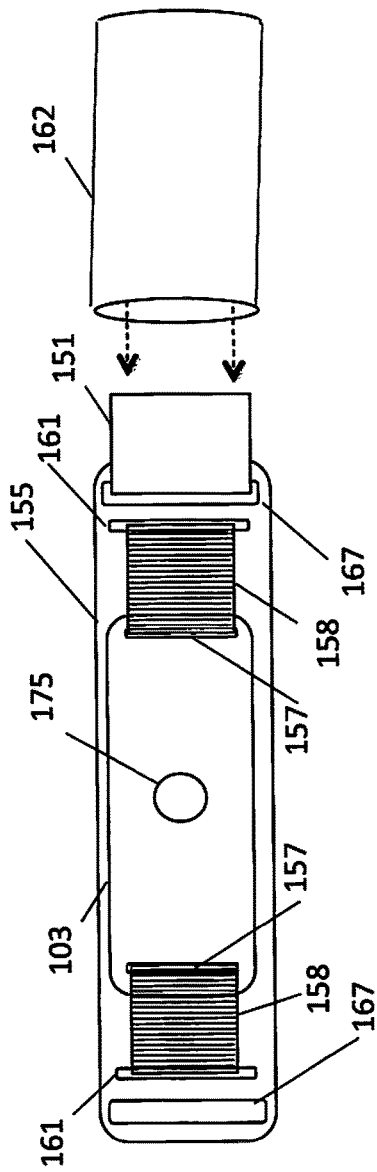
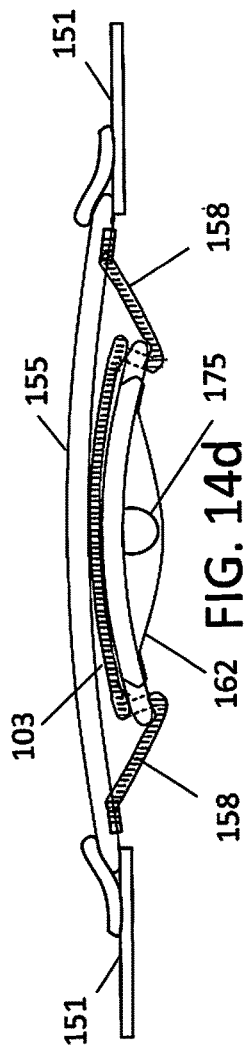
FIG. 14c
FIG. 14d

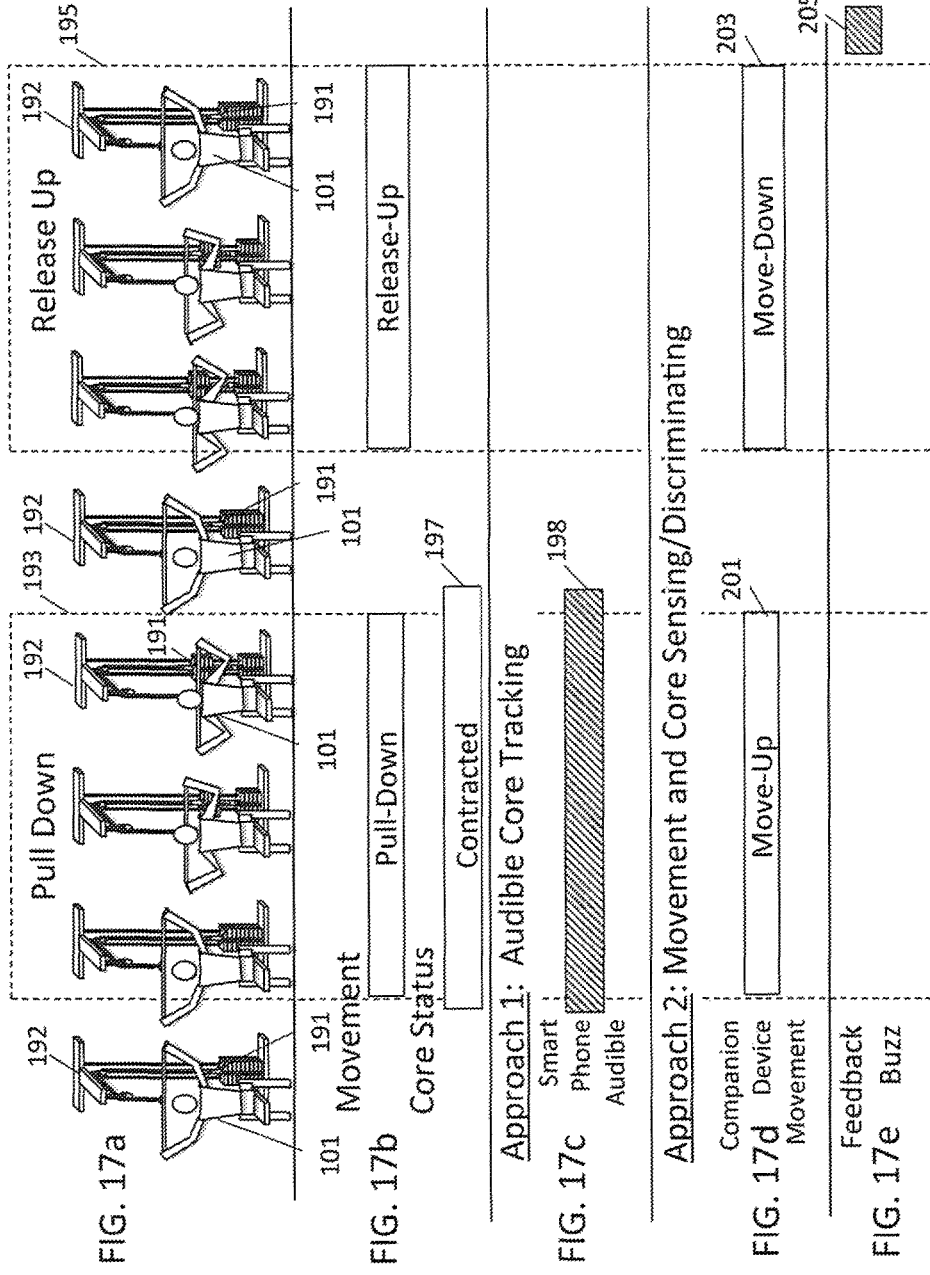

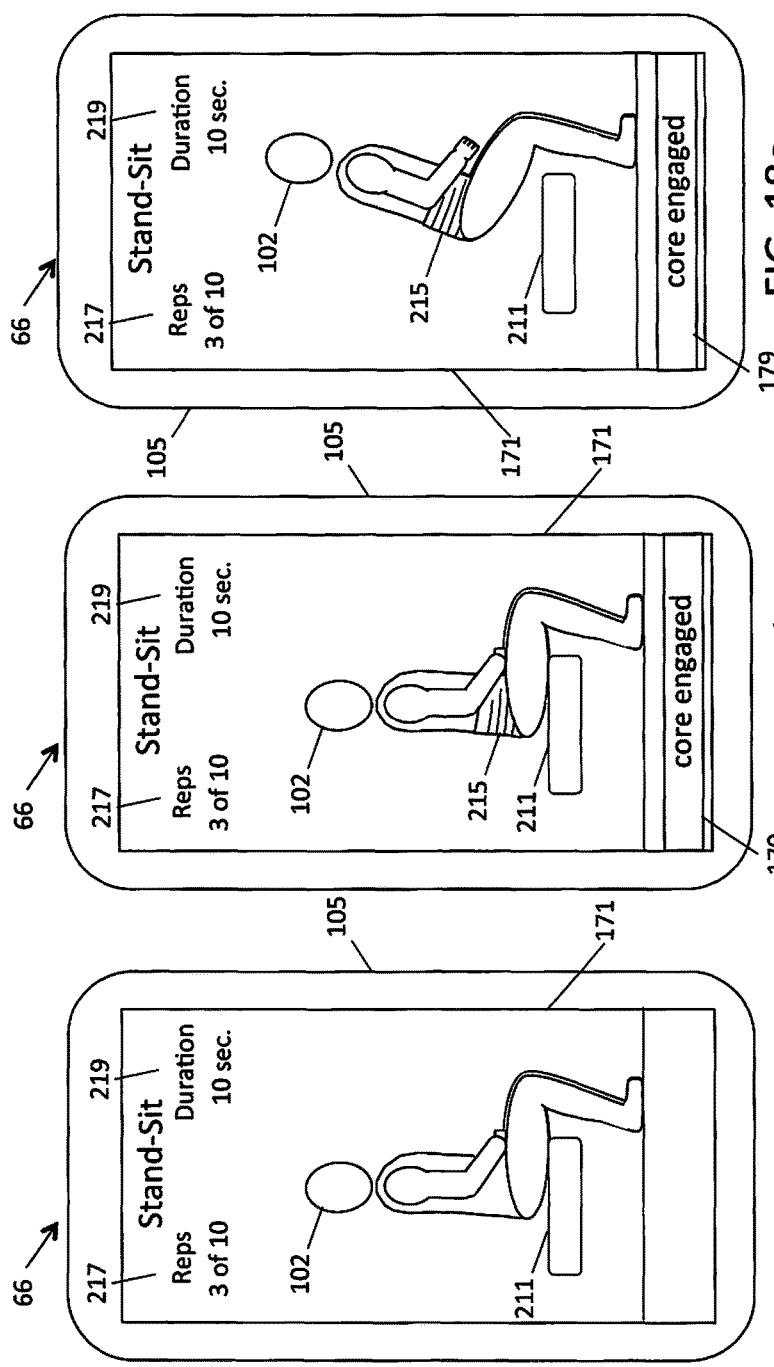

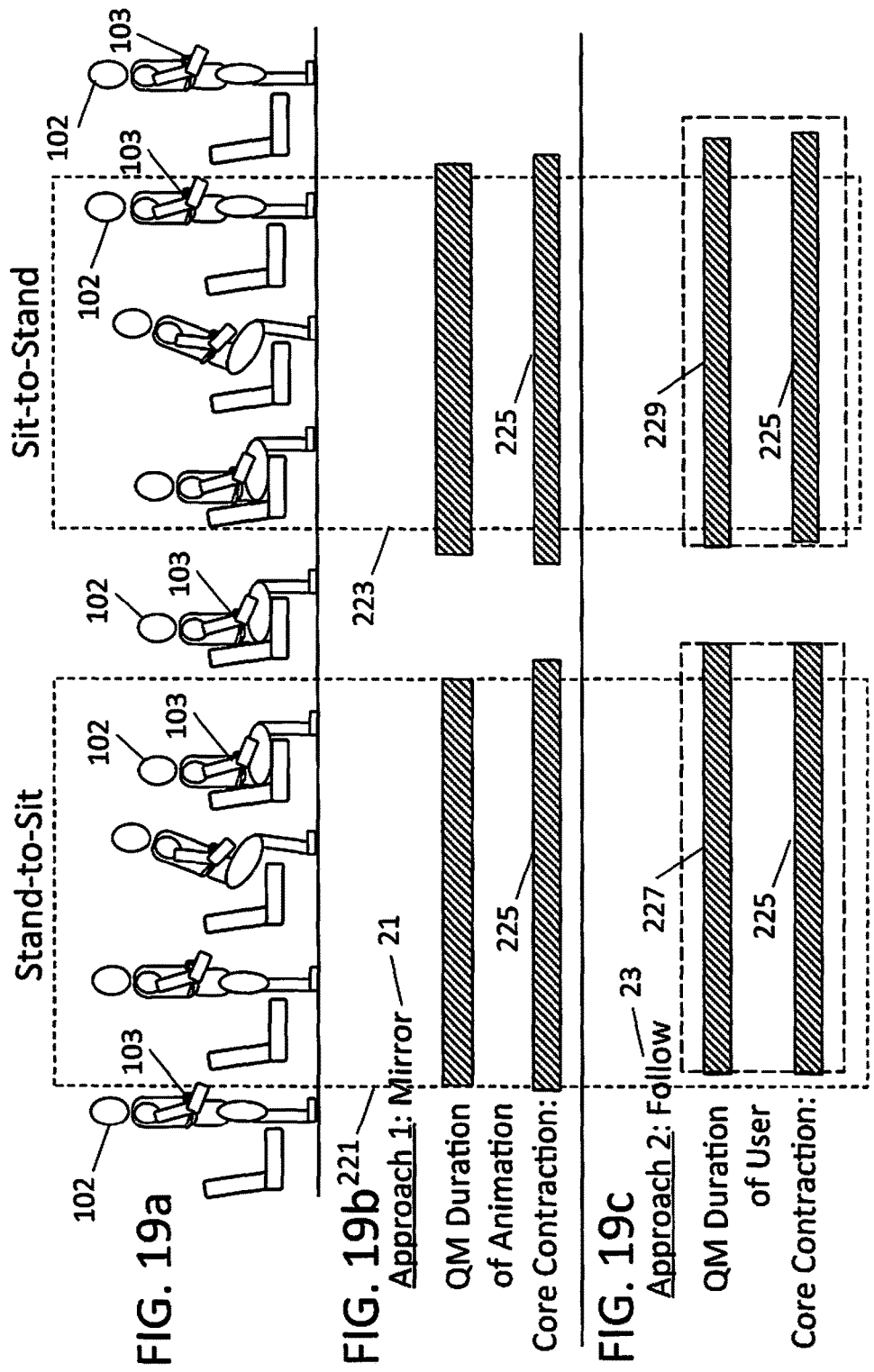

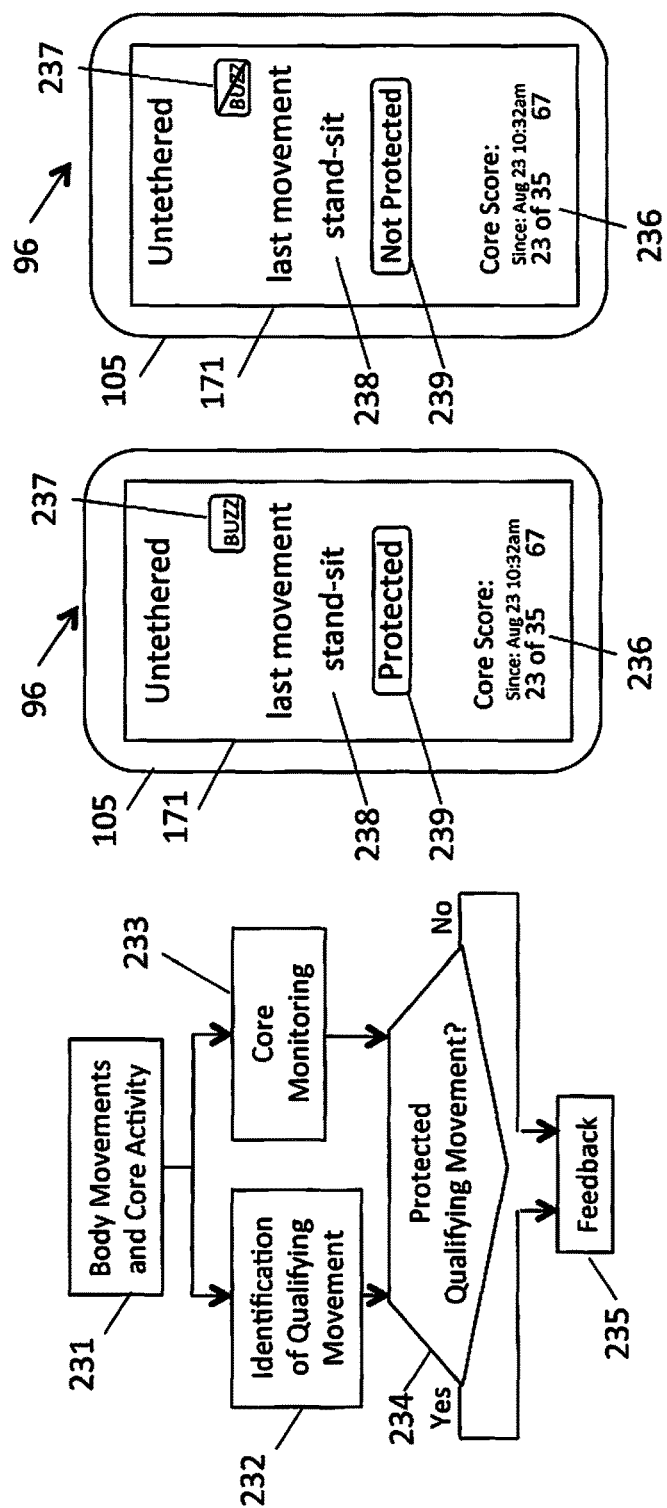

| Use No. | Location | Application | Additional Devices | Description |
|---|---|---|---|---|
| 1 | In-Session | Therapist and User focus on isolated core teaching using Core Contraction Feedback | Smart Phone (in some applications) | Provides User and Therapist with feedback on core status; may identify hollowing vs. bracing |
| 2a | In-Session | User on exercise equipment in Therapist's gym using Core Contraction Feedback | Smart Phone (in some applications) | Enables monitoring and feedback of core status during exercise movements |
| 2b | In-Session | User on exercise equipment in Therapist's gym using Qualifying Movement Feedback | Companion Device (ID machine movements) | Enables monitoring and feedback of core status timing with respect to exercise movements |
| 3 | Out-of-Session | At Home Practice: User and smart phone app using both Core Contraction Feedback and Qualifying Movement Feedback | Smart Phone (coaching + feedback) | User follows video teaching clips while sensors monitor movements and core status and receives feedback |
| 4 | Out-of-Session | Untethered; Buzz on unprotected movements using Qualifying Movement Feedback | None | Device monitors movements and core contraction and provides feedback |

FIG. 21

WEARABLE DEVICE AND SYSTEM FOR TEACHING CORE USAGE AND RELATED APPLICATIONS

CROSS-REFERENCE TO RELATED APPLICATIONS

This application claims priority to U.S. Patent Application No. 62/032,664, "Wearable Device And System To Support Therapist Teaching Core Usage And Related Applications" filed Aug. 4, 2015. This application is a continuation-in-part of U.S. patent application Ser. No. 14/132,808 entitled "System, Apparatus, And Method For Promoting Usage Of Core Muscles And Other Applications", filed Dec. 18, 2013, which claims priority to U.S. Provisional Application No. 61/739,160, entitled "System For Promoting Usage Of Core Muscles And Other Applications", filed Dec. 19, 2012. This application is a continuation-in-part of U.S. patent application Ser. No. 14/789,136 "Apparatus And Method For Teaching And Algorithms For Identifying Qualifying Movements", filed Jul. 1, 2015 which claims priority to U.S. Provisional Application No. 62/027,409 entitled "Apparatus And Method For Teaching And Algorithms For Identifying Qualifying Movements", filed Jul. 22, 2014, and also claims priority to U.S. Provisional Application No. 62/019,522 entitled "Apparatus And Method For Teaching And Algorithms For Identifying Qualifying Movements", filed Jul. 1, 2014. This application is a continuation-in-part of U.S. patent application Ser. No. 14/800,931 "Companion Device To Support Qualifying Movement Identification" filed Jul. 16, 2015 which claims priority to U.S. Provisional Application No. 62/025,929 entitled "Companion Device To Support Qualifying Movement Identification", filed Jul. 17, 2014. The disclosures of U.S. patent application Ser. Nos. 14/132,808, 14/789,136, 14/800,931, 61/739,160, 62/019,522, 62/025,929, 62/027,409 and 62/032,664 are incorporated herein by reference in their entirety.

FIELD OF THE INVENTION

Embodiments disclosed relate to systems, methods, and devices for development of support from core muscles by identifying user movements, and by detecting core muscle usage in conjunction with those identified movements. Embodiments also relate to discriminating between multiple identified movements, recognizing core muscle activity or lack of it thereof in those identified movements, and providing feedback to the user regarding a correct or incorrect core muscle use, acknowledging a core muscle use when appropriate, informing of an inappropriate core muscle use, and identifying a movement wherein a core muscle is not used but could be used. Embodiments relate to a companion device that may operate with a wearable device to encourage core usage when exercising and training with exercise equipment. Embodiments also relate to use of the companion device that may operate together with the wearable device to encourage coordinating core usage with body movements associated with movements in sports and athletics. Embodiments relate to a wearable device and system to support the encouragement and development of procedural memory for core support of the lumbosacral junction before and during movements. Embodiments relate to a wearable device and system to supplement teaching and instruction by a therapist such as a physical therapist for aiding treatment of and protecting against low back pain and other related body ailments.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be embodiments of the invention.

Many in healthcare, sports, and fitness and movement disciplines teach core strengthening as an integral part of treatment and training regimens. Many of these therapists, coaches, teachers, and trainers (let us refer to these groups as therapists) emphasize core training in order to both protect against back pain as well as treat back pain. There are a large number of exercises, strategies, programs, and approaches to strengthening the core muscles. However, there are very limited tools used by such therapists to help clients/patients/athletes/students (let us refer to these as clients) to develop the habit of using their core before and during movements to support the lumbosacral junction.

Let us define a Qualifying Movement or QM as a movement for which support from the contraction of the core muscles may be beneficial to support and protect the lumbosacral junction and the lumbar spine. Furthermore, let us define QM Identification or QM ID as the method, process, principles, approach and/or concepts utilized to evaluate the available data to make a determination whether or not a user utilizing the inventive system has executed a Qualifying Movement.

U.S. patent application Ser. No. 14/132,808 includes the description of an inventive system comprising a wearable device which monitors a user's movements for Qualifying Movements and the user's core muscles for contraction of the core. When a Qualifying Movement is identified, based on the status of the user's core before, during, and after the Qualifying Movement, the system may determine whether or not the Qualifying Movement is protected or not protected. If the user's core is contracted adequately during the movement, the Qualifying Movement may be determined to be protected. If the core is not contracted adequately during the Qualifying Movement, the movement may be determined to be not protected. Based upon the result of the determination of the movement being protected or not protected, the system may signal to the user in order to aid the user in developing procedural memory to utilize their core to protect their lumbar spine and lumbosacral junction during such Qualifying Movements.

U.S. Provisional Patent Application Nos. 62/027,409 and 62/019,522 includes the description of an inventive teaching approach for users to develop said procedural memory for core support while performing every day movements. In addition, a comprehensive approach for algorithm development and implementation for identifying Qualifying Movements in every day movements which operate on the outputs of sensors contained in a wearable device is described.

U.S. Provisional Patent Application No. 62/025,929 includes the description of: a. Companion device that may be attached to different attachment mechanisms or attachment devices such as a wrist strap; and b. Extension of the comprehensive approach for algorithm development and implementation for Qualifying Movement Identification described in U.S. Patent Application No. 62/019,522 to systems employing the wearable device described in U.S. patent application Ser. No. 14/132,808 and embodiments of the companion device.

The role of the core muscles for stabilizing the region of the lumbosacral junction during certain movements is widely encouraged by a number of disciplines including physical therapy, occupational therapy, personal training, strength training, fitness training, crossfit, yoga, pilates, and tai-chi. The stabilizing role of the core muscles has also been identified to be critical in athletics to add strength and power.

In some physical therapy practices and/or sessions, therapists may have their clients perform exercises as part of the rehabilitation process. Sometimes, these exercises are performed on the same or similar exercise machines often found in exercise and gym facilities. When rehabilitating back pain, one of the procedures physical therapists may have their clients perform is to contract their core muscles during the exertion portions of exercises. There are at least two advantages to utilizing the core during exercise movements. First, the lumbosacral junction and lumbar spine is supported during the exercises. This may limit the possibility of any or further injury while strengthening the muscles being exercised. And second, the client may practice utilizing their core during movements where their muscles are lightly, moderately, to heavily loaded and develop procedural memory to utilize their core muscles in similar movements, and particularly Qualifying Movements. Many physical therapists encourage their clients to contract their core prior to and during movements including movements such as sit-to-stand (sitting down from a standing position) and stand-to-sit (standing up from a sitting position). Many of the teaching practices used by physical therapists as just described may also be used by other disciplines including occupational therapist, physiatrists, chiropractors, and personal, fitness, and strength trainers.

Emphasizing and monitoring core contractions during exercise requires a highly interactive session between a therapist and a client in order to continually remind the client and monitor the client to contract their core muscles before and during movements. Due to practical difficulties such as placing a hand on the client's core in the abdomen region while the client is moving, such monitoring is seldom done due to the inconveniences. So while the objective of monitoring the core muscles during gym exercises and providing feedback to the client, particularly when they fail to utilize their core muscles during exercise movements is desirable, it generally is not done, in part, due to the lack of availability of effective and convenient tools, devices, or systems.

A summary of desirable elements and features in a tool, device, or system for teaching and learning to use the core muscles to support the lumbosacral junction and lumbar spine during movements may include:

A. Relatively low cost tool or tools in the form of a device and system to help a therapist train a client how to contract their core muscles and to know when the core is contracted;

B. Said device and system with the ability to differentiate between a contraction and an inward movement of the abdominal muscles vs. a neutral or outward movement of the abdominal muscles on contraction in order to teach a therapist's preference of abdominal hollowing vs. bracing;

C. Said device and system that allows identification of core muscles contracting while a client performs gym exercises during a therapy session;

D. Said device and system that can be used during the therapy session and used outside the therapy session to encourage usage of the core muscles during movement while performing every day movements and activities;

E. Said device and system that allows a client to practice core contraction with every day movements from their home or outside of the therapist's office in order to develop procedural memory for core usage during movements;

F. Said device and system that allows a client to track their movements to identify Qualifying Movements, as well as track their core muscles and provide feedback to notify the client (or user) of protected or unprotected qualifying movements in order to develop procedural memory for core usage during movements; By having such a device and system, the continual practice may help a user more quickly develop the new habit of using their core before and during movements;

G. Said device and system to maintain a quantitative score to encourage and track usage of the core muscles during Qualifying Movements.

Elements of the inventive devices and systems described in aforementioned patent and provisional patent applications contain the desirable elements and features listed above. In this disclosure, a more complete and systematic description of some of the features of the inventive devices and systems are presented. More detail is provided on how the In-Session and Out-of-Session models may be utilized and supported, both by the therapist and the client. Furthermore, additional inventive steps and features such as methods to fit the wearable device to a user along with descriptions of related apps running on a smart phone or smart device are described.

Throughout this disclosure, a standard ubiquitous communication protocol such as Bluetooth is assumed. More specifically, Bluetooth Low-Energy or BLE may be utilized. Appropriate procedures for pairing devices, for example the wearable device to a smart phone or smart device, or the companion device to the wearable device is assumed. Other communication protocols may be similarly utilized.

BRIEF DESCRIPTION OF THE DRAWINGS

FIG. 1a illustrates an embodiment of an in-session scenario with a therapist holding a smart device and a user wearing the wearable device.

FIG. 1b illustrates an embodiment of an out-of-session scenario with the user wearing the wearable device and holding a smart device while practicing with an exercise app.

FIG. 1c illustrates an embodiment of an out-of-session scenario with the user wearing the wearable device.

FIG. 6a illustrates a side view of an embodiment of the wearable device and core sensor interface.

FIG. 6b illustrates a front view of an embodiment of the wearable device and core sensor interface.

FIG. 6c illustrates a top view of an embodiment of the wearable device and core sensor interface showing an internal compartment to house electronics, sensors, and a battery.

FIG. 6d illustrates a top view of an embodiment of the wearable device and core sensor interface attached to a belt.

FIG. 6e illustrates a front view of an embodiment of the wearable device and core sensor interface attached to a belt.

FIG. 6f illustrates a top view of an embodiment of the wearable device and core sensor interface attached to a strap with the strap attached to a belt.

FIG. 7a illustrates a front view of an embodiment of the wearable device and core sensor interfaces utilizing two nodes for core contraction sensing.

FIG. 7b illustrates a top view of an embodiment of the wearable device and core sensor interfaces utilizing two non-protruding sensing nodes.

FIG. 7c illustrates a top view of an embodiment of the wearable device and core sensor interfaces utilizing two protruding sensing nodes.

FIG. 8a illustrates a front view of an embodiment of the wearable device and core sensor interfaces for core contraction sensing having a transmitter and a receiver.

FIG. 8b illustrates a top view of an embodiment of the wearable device and core sensor interfaces for core contraction sensing using non-protruding sensor interface structures having a transmitter and a receiver.

FIG. 8c illustrates a top view of an embodiment of the wearable device and core sensor interface for core contraction sensing using a combined protruding sensor interface structure having a transmitter and a receiver.

FIG. 11a illustrates an embodiment of a bumper with an extender cap.

FIG. 11b illustrates a perspective view of an embodiment of a bumper with an extender cap.

FIG. 11c illustrates an embodiment of a bumper with an extender cap placed on the bumper.

FIG. 11d illustrates an embodiment of a bumper with an additional cavity and an extender cap with an additional extrusion to fit into the additional cavity in the bumper.

FIG. 11e illustrates an embodiment of the bumper and the extender cap placed on the bumper.

FIG. 13a illustrates a cross sectional view of an embodiment of the device, bumper, and belt on a user with prominent hip bones.

FIG. 13b illustrates a cross sectional view of an embodiment of the device separating from the adjoining line and toward the core muscles.

FIG. 13c illustrates a cross sectional view of an embodiment of the device with a strap connecting both ends of a belt and gap extenders connecting to the device to enable the device to separate from the adjoining line toward the core.

FIG. 13d illustrates a cross sectional view of an embodiment of the device with a gap filler for holding the device against the core on a user with prominent hip bones.

FIG. 14a illustrates a top view of a cross section of an embodiment of the device, bumper, strap, gap extender, and belt.

FIG. 14b illustrates a front view of an embodiment of the device, bumper, strap, gap extender, and belt.

FIG. 14c illustrates a front view of an embodiment of the device, bumper, strap, gap extender, and belt with a tubular shaped material to slide over the device and bumper.

FIG. 14d illustrates a top view of a cross section of an embodiment of the device, bumper, strap, gap extender, and belt with a tubular shaped material positioned over the device and bumper.

FIG. 17a illustrates a user on a lat pull-down machine performing a repetition of the exercise.

FIG. 17b illustrates time bars indicating periods of movements and the core status indicating when the core is contracted.

FIG. 17c illustrates an embodiment of showing the times an audible signal may be present to reflect identification of a core contraction.

FIG. 17d illustrates an embodiment utilizing movement and core sensing with discriminating including a companion device and indicating the movement of the companion device.

FIG. 17e illustrates an embodiment of the timing of a buzzer for the embodiment shown in FIG. 17d.

FIG. 18a illustrates a screen shot of an embodiment of the Stand-Sit app showing the number of reps, the duration for each rep, and a seated user.

FIG. 18b illustrates a screen shot of an embodiment of the Stand-Sit app showing the number of reps, the duration for each rep, a seated user with core contracted before starting a movement, and a core engaged indicator.

FIG. 18c illustrates a screen shot of an embodiment of the Stand-Sit app showing the number of reps, the duration for each rep, a seated user with core contracted and moving to the stand position, and a core engaged indicator.

FIG. 19a illustrates a user performing a repetition of the stand-sit exercise.

FIG. 19b illustrates an embodiment of mirror mode with the QM duration and core contraction timing identified where QM duration mirrors that of the animated figure.

FIG. 19c illustrates an embodiment of follow mode with the QM duration and core contraction timing identified where QM duration follows that of the user.

FIG. 20a illustrates an embodiment of a flow chart for identifying feedback for a protected or unprotected qualifying movement starting with a user's movements and core activity.

FIG. 20b illustrates a screen shot of an embodiment of the Untethered app showing the buzz option selected, last qualifying movement identified as a stand-sit, the last qualifying movement identified as a protected qualifying movement, and Core Score data.

FIG. 20c illustrates a screen shot of an embodiment of the Untethered app showing the no buzz option selected, last qualifying movement identified as a stand-sit, the last qualifying movement identified as a not protected qualifying movement, and Core Score data.

FIG. 21 illustrates a table of an embodiment of use models for in-session and out-of-session usage.

DETAILED DESCRIPTION

Figure 2:
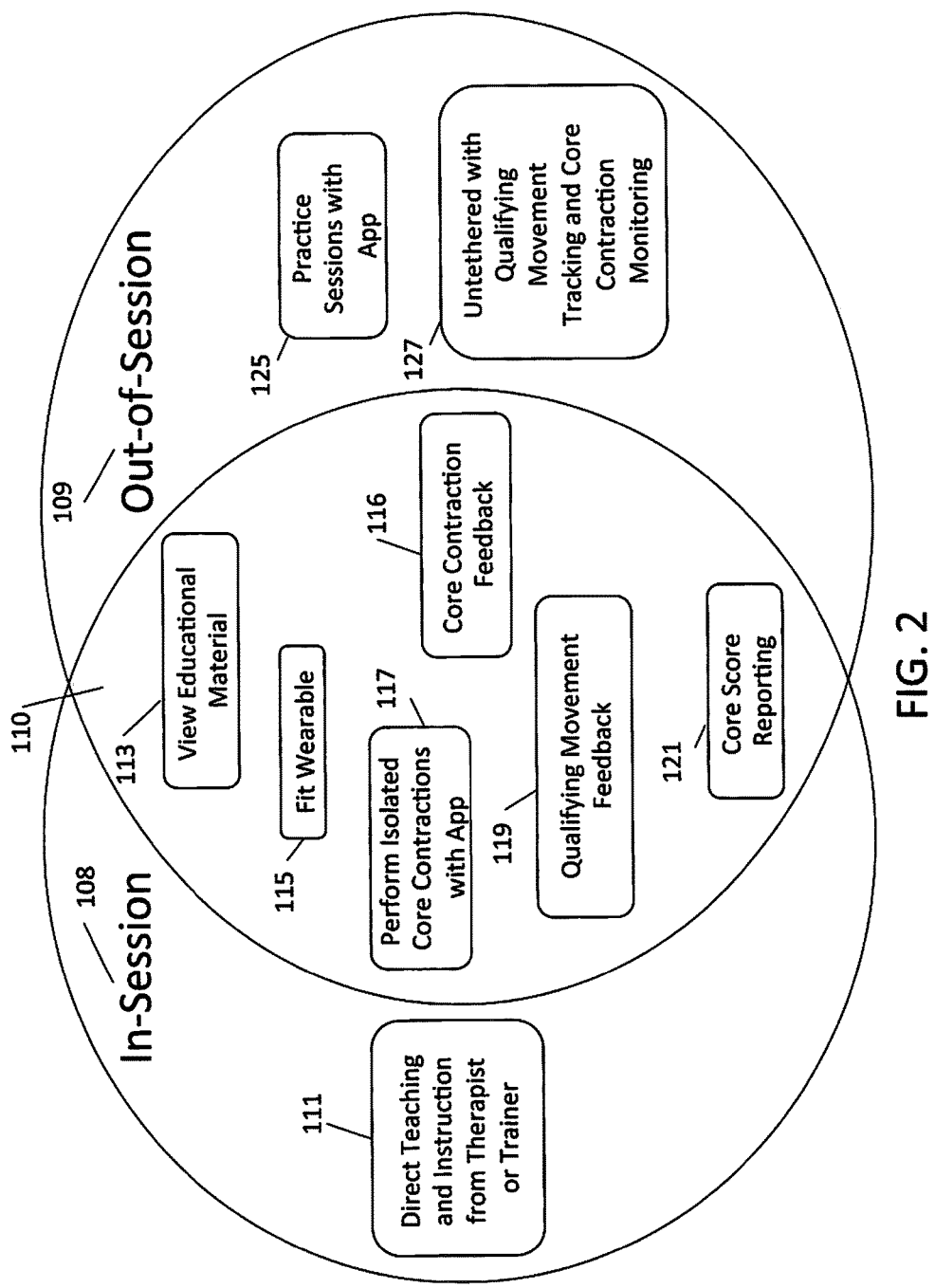
FIG. 2 illustrates an embodiment of in-session, out-of-session, and joint model uses Venn diagram.

The development of procedural memory to contract the core muscles in order to protect the lumbar spine and lumbosacral junction during qualifying movements may benefit from repetition, that is, the regular practice of performing protected qualifying movements. Aspects of this invention emphasize and expand on the continuity from In-Session and Out-of-Session use models of the inventive wearable device and system described in the aforementioned patent application and provisional patent applications. In-Session refers to use of the device and system with a therapist, trainer, teacher, coach or doctor during a session that may be a weekly meeting, or a meeting twice or more per week. This lead person will be referred to as therapist in this description. A more specific example of a therapist may be a physical therapist or an occupational therapist. Out-of-Session refers to use of the device and system by the user, user of the system, client, or client of the therapist outside of a formal therapy or training session. For example, out-of-session may refer to the use of the system while the user is at their place of residence. A person learning to use and develop procedural memory to use their core muscles to protect their lumbar spine and lumbosacral junction during qualifying movements will be referred to as user in this description.

Examples of the use model In-Session 108 and Out-of-Session 109 are shown in FIG. 1. In FIG. 1a, a therapist 107 is depicted as holding a smart phone (equivalently smart device) 105 while the user 101 is shown wearing a wearable device 103 in a depiction of an in-session 108 scenario. As the therapist 107 is teaching the user 101 to contract their core, the wearable device 103 worn on a belt near the waist on the core muscles is detecting the core contraction and providing immediate or substantially immediate feedback through the smart phone 105. For example, the smart phone 105 may provide feedback via sound or image to both the therapist 107 and the user 101. Out-of-Session 109 use models are depicted in FIGS. 1b and 1c. In FIG. 1b, the user 101 may be performing an exercise of stand-sit while practicing to contract their core muscles before and during the movements following an exercise app. The exercise app may be displayed on a smart phone or smart device 105 via a video clip or an animated clip with instruction. The wearable device 103 may provide feedback to the smart device 105 as to whether the user 101 is properly contracting their core with respect to timing of the movements. The user 101 may be encouraged to perform a series of exercise apps, one or more times per day. Another use of the out-of-session 109 model is untethered, where the wearable device 103 may be used without the smart device 105. In this mode, the user's 101 movements may be tracked using the wearable device 103 sensors and algorithms identifying Qualifying Movements and monitoring the user's core for contractions Based on the timing of the Qualifying Movements and core contractions, feedback may be provided. For example, if the algorithms detect that a Qualifying Movement is not protected (or unprotected), the wearable device 103 may buzz. The wearable device 103 may keep track of the number of Qualifying Movements and the number of Qualifying Movements that are protected, which will allow later reporting of the Core Score which is a measure of the percent of opportunities the user 101 contracts their core during Qualifying Movements.

In FIG. 2, two overlapping circles are shown representing the In-Session 108 and Out-of-Session 109 use models. Some of the uses 110 may be applied or utilized both In-Session 108 and Out-of-Session 109. Let us now describe each of the boxes in detail.

Direct Teaching and Instruction 111—

Direct teaching and instruction 111 may be possible In-Session 108 with the therapist 107 present for teaching and instruction. Each of the items in the figure may be addressed, taught, and run through with the therapist 107. Learning to use the core muscles properly and on cue or when desired, are skills that may take a user 101 time to develop. Direct teaching 111 may allow a therapist the opportunity to introduce, develop, and improve the way a user 101 utilizes their core muscles with a high degree of detail.

View Educational Material 113—

Educational material may be studied and viewed 113 outside of the formal session. However, there may be high value in having the therapist 107 explain some foundational information regarding basic anatomy, role of the core muscles for supporting and protecting the lumbar spine, and approaches or techniques for using the core muscles.

Fit Wearable 115—

Proper fitting 115 of the wearable device 103 to the user 101 is important to achieve good sensitivity for identifying contraction and relaxation of the core as well as wear-ability and comfort.

Perform Isolated Core Contractions with App 117—

Contracting the core muscles to protect the lumbar spine may be a new activity to new users of the system; one approach to learn this is to perform core contractions in isolation 117, that is, in the absence of other movements. The app running on the smart device 105 may include exercises that may be diagrammatic, video clips, or animations to teach isolated core contractions with identifying how and when the core may be contracted and when the core may be relaxed. The user may be encouraged to run at least one of these practice apps each day.

Core Contraction Feedback 116—

The inventive system may be programmed to provide feedback to the user 101 when the user's 101 core is detected to be contracted as described in previous patent applications. Core contraction feedback may be provided by the wearable device 103, the smart device 105, a companion device, another external device, or combinations of devices. The feedback signal may take on many forms depending on which device is providing the feedback and the available output devices. With core contraction feedback 116, the feedback signal provided may be associated with a contracted core or a relaxed core. In an embodiment, the feedback signal may be provided in association with a contracted core and no feedback signal may be provided with a relaxed core. Core contraction feedback 116 may be used with isolated core contractions with an app 117, sequenced exercises with an app, core contraction instruction with a therapist 107, gym exercises, exercise and training movements, sports and athletic movements, movements and held positions in movement disciplines, occupations involving lifting, and core tracking during movements throughout the day and night. Examples of movement disciplines include pilates, yoga, tai chi, chirunning, and dance. Examples of occupations involving lifting include airline baggage handlers and airline check-in personnel, warehouse stocking personnel, shipping dock workers, and carpenters, Core contraction feedback 116 may be used in other applications.

Qualifying Movement Feedback 119—

The inventive system may be programmed to provide feedback to the user 101 when the system identifies a qualifying movement and a user's 101 core status before and during the qualifying movement, and may provide feedback whether the qualifying movement was protected or not protected as described in previous patent applications. Qualifying movement feedback 119 may be provided by the wearable device 103, the smart device 105, a companion device, another external device, or combinations of devices. The feedback signal may take on many forms depending on which device is providing the feedback and the available output devices. In an embodiment, the feedback signal may be provided in association with an unprotected qualifying movement and no feedback signal may be provided with a protected qualifying movement. A qualifying movement may be identified by the wearable device 103, a companion device, another external device, or combinations of devices. Qualifying movement feedback 119 may be used with sequenced exercises with an app, gym exercises, exercise and training movements, sports and athletic movements, movements and held positions in movement disciplines, occupations involving lifting, and untethered tracking of movements throughout the day and night. Qualifying movement feedback 119 may be used in other applications.

Core Score Reporting 121—

The inventive system may identify qualifying movements with body movements such as stand-sit and sit-stand. Furthermore, with the use of a companion device, it may identify exercise movements that may also be identified as qualifying movements. Monitoring the core muscles during the qualifying movements and determining whether the qualifying movements are protected or not protected may allow a core score to be reported 121 to both the user 101 and the therapist 107.

Practice Session with App 125—

The app running on the smart device 105 may include exercises that may be diagrammatic, video clips, or animations to teach qualifying movements with identifying when the core may be contracted and when the core may be relaxed. The user may be encouraged to run at least one of these practice apps each day.

Untethered 127—

In untethered mode 127, the wearable device 103 may operate without a smart phone app. In this mode, using movement sensors contained in the wearable device 103, body movements may be monitored to identify Qualifying Movements and the core for core contractions. Each identified QM and core contractions data may evaluated as to whether or not the QM is protected or unprotected. A record of protected and unprotected qualifying movements may be stored and reported to the app running on the smart device 105 at a later time after the wearable 103 becomes tethered again. The data reported by the app to the user 101 may include the Core Score 121. Untethered mode 127 may utilize qualifying movement feedback 119.

The elements described in FIG. 2 are examples of learning, training, and motivational elements enabled by the inventive system. Additional elements are possible and may be used in combination with the elements just described. We will now examine further some of the elements just described in order to add additional detail and present additional inventive elements of the inventive system.

Figures 3A, 3B, 3C:
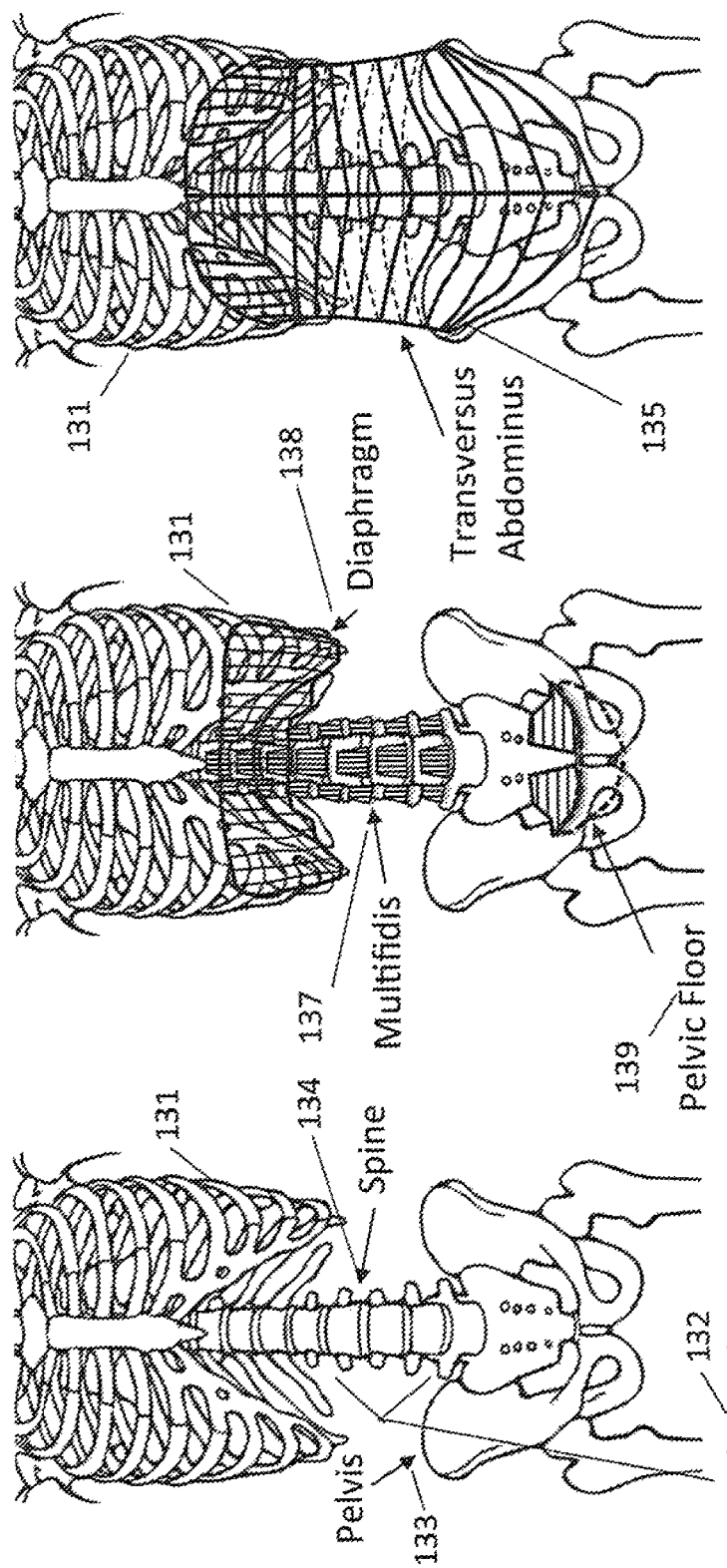
FIG. 3a illustrates the torso area of a human skeleton.
FIG. 3b. illustrates the Multifidis, Diaphragm, and Pelvic Floor.
FIG. 3c. illustrates the Transversus Abdominus.
Figure 4B:
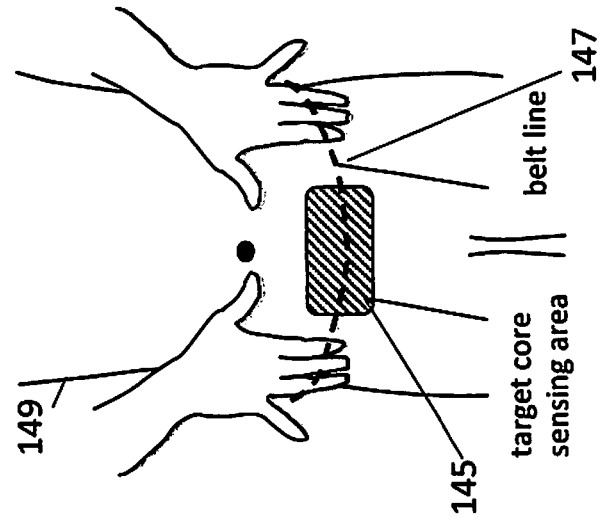
FIG. 4b illustrates an embodiment of the target core sensing area for placement of the wearable device.
Figure 4A:
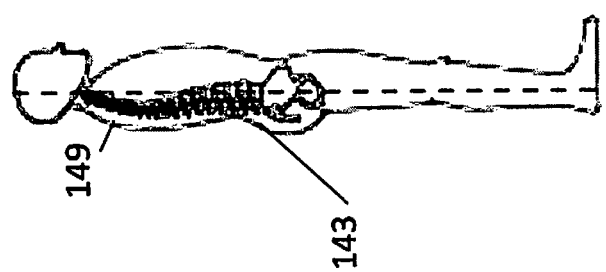
FIG. 4a illustrates a human body outline with the spine and pelvis showing an S-curve.

Teaching material may include an introduction to the human skeleton 131, concentrating on the physical structures in the region where the spine 134 the pelvis 133 connect and how the nerves from the spine are passed through the lumbar spine. Furthermore, the role of the core muscles to stabilize this region of the lumbosacral junction as well as the lumbar spine during body movements may be explained or taught with written text, or by animations and video clips using with images similar to those shown in FIGS. 3*a*-3*c*. The so-called inner core muscles including the transversus abdominus 135, multifidis 137, diaphragm 138, and pelvic floor 139 are shown in FIGS. 3*b*-3*c* and may be an important part of foundational teaching of the core muscles. Additional educational content may include the role of posture using an image similar to that shown in FIG. 4*a* which includes the well known S-curve shape of the spine 143 inside an outline of the human body 149. Another important illustration in the educational portion of the app is shown in FIG. 4*b* and may include a preferred location for the wearable device in an embodiment referred to as the target core sensing area 145. A description of one way to identify the deepest and one of the more important core muscles called the transversus abdominus is shown by illustrating the placement of fingers near the belt line in FIG. 4*b*. An accompanying description of exhaling and evacuating the lungs of as much air as possible through a series of pushes from the core section of the body, enabling the firmness of the contracted transversus abdominus to be felt by the fingers in the position shown in FIG. 4*b* may be desirable in the description. These are merely examples of the information content that may be provided as educational material. While the inventive system may support making the connection from the brain to the core through practice exercises, an understanding of the underlying anatomy may help to strengthen the understanding and motivation for a user 101.

Some important design aspects of the wearable device 103 will now be examined and examples of adjustable parameters will be identified. With some key adjustable parameters identified, examples of how a wearable 103 may be fitted to a user 101 to meet the objectives of sensitivity for identifying core contraction and comfort will be presented.

Figure 5B:
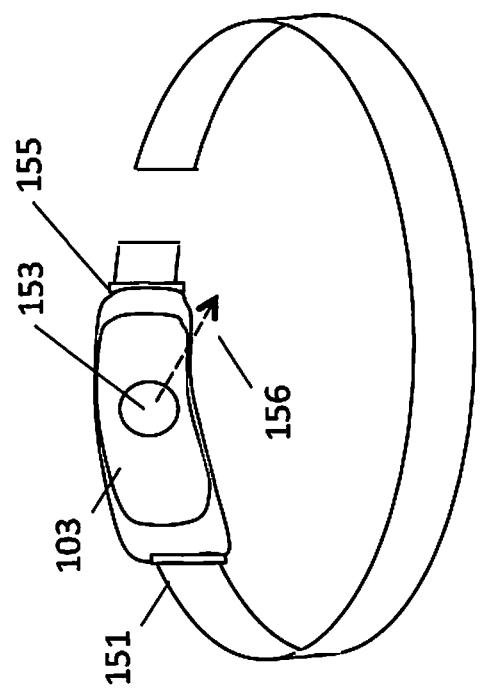
FIG. 5b illustrates an embodiment of a core sensor interface and a wearable device attached to a strap coupled to a belt.
Figure 5A:
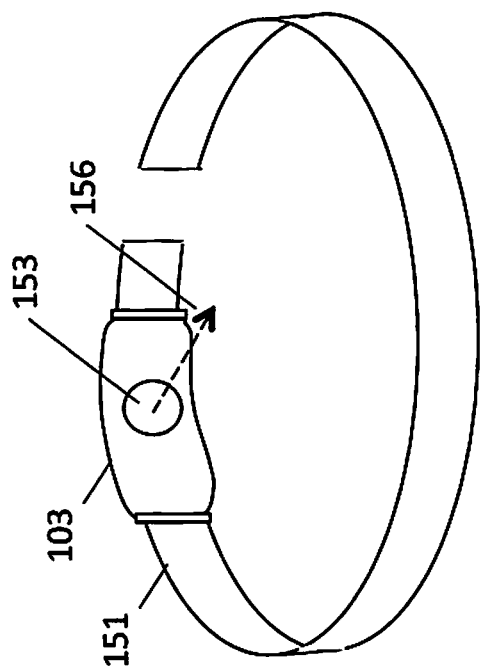
FIG. 5a illustrates an embodiment of a core sensor interface and a wearable device attached to a belt.

An embodiment of the wearable device is shown in FIG. 5*a* including a core sensor interface 153, device 103, and belt 151. The core sensor interface 153 may couple to the user's 101 core muscles in the direction shown by the arrow. The device 103 may include a printed circuit board (PCB) and may contain sensors, a processor, power management electronics, communication electronics, and a battery. The belt 151 may be adjustable in length. In an embodiment, the belt 151 may have at least a portion of a length that is elastic. In another embodiment, the belt 151 may be substantially elastic. In another embodiment, the belt 151 may have no portion that is elastic.

Details of the sensor interface 153 will depend on the specific type or types of sensors used to monitor the core muscles. Some users 101 may have core muscles that are more developed while others may have core muscles that are less developed. Some users may have more body fat over the core muscles while others may have less body fat over the core muscles. In an embodiment, the sensor interface may extrude from the face of the device 103 and may be referred to as a bumper. In an embodiment, the bumper may couple to the core muscles. In an embodiment, the bumper may have a variable height to accommodate variations from user to user in the amount of body fat over the core muscles as well as differing amounts of core muscle development. In an embodiment, the bumper may couple to the user's 101 core muscles in the target core sensing area 145. The inner core muscles generally co-contract, meaning the muscles contract together. While the target core sensing area 145 is an attractive location for attaching the wearable device 103, other locations may be utilized. For example, when the transversus abdominus 135 contracts, the diaphragm 138 may also contract. In an embodiment, the location of the solarplexus below the lungs, between the ribs, and above the abdominal section may be used as the attachment location of the wearable 103.

Another embodiment is shown in FIG. 5b. The primary difference compared with the embodiment shown in FIG. 5a is the device is attached to an additional element we may refer to as a strap 155. The strap may then connect to the belt 151. The strap may bring benefits to the inventive system that will be described later. Some embodiments of the wearable device 103 may be attached with a belt with a means to control a variable length of the belt 151. Fitting the wearable device may include modifying the adjustable elements to achieve a preferred combination of sensitivity and comfort.

As described in U.S. patent application Ser. No. 14/132,808, a number of technologies may be used in core sensing to identify a core contraction. For example, a force sensor or pressure sensor may be used. By applying pressure to a device attached against the core muscles, engagement or contraction of the core muscles may result in a pressure change on the device which may be detected by a force sensor or pressure sensor. An embodiment of the device utilizing a force sensor is shown in FIG. 6. In another embodiment, movement sensors may be utilized to detect movements associated contraction of the core muscles. In another embodiment, electromyography or EMG or other sensing techniques utilizing similar principles may be utilized. Electrical current flows into a muscle in order to contract the muscle, and this current may be detected with electrical sensors. The current may be detected by measuring a voltage difference between two points on the skin. In an embodiment of EMG, fine needles may be placed into the muscles being tested. The use of needles directly into the muscles may be more accurate than monitoring the muscles from the surface of the skin. However, needles are quite intrusive for a system that may be used in a variety of settings and by users with little training on how to attach and remove needles. An embodiment of the device utilizing voltage sensing or principles of EMG using sensing on the skin is shown in FIG. 7. In another embodiment, the principles of backscattering may be used. In backscattering, a source signal is transmitted by a transmitter and the reflection of the signal back in the direction from which it was transmitted is measured by a receiver. When the core muscles are contracted, blood flows to the muscles, resulting in changes in the reflected signal. These changes may be identified and associated with core muscle contraction. A number of different types of signals may be used. For example, ultrasound, infrared, and electromagnetic energy may be used. An embodiment of the device utilizing backscattering is shown in FIG. 8. In other embodiments, other sensing technologies may be used. Appropriate modifications may be needed to the system to accommodate specific details associated with the implementation of different techniques and technologies.

An example of the system utilizing a force sensor in the form of a force sensing resistor or FSR is shown in FIG. 6 and will now be examined in more detail. The side view of the device 103 is shown in FIG. 6a, the front view of the device 103 which is the side of the device which will press up against the user's core enabling the core sensor interface 153 to couple to the user's core is shown in FIG. 6b. The top view of the device is shown in FIG. 6c. The curve shown in FIG. 6c may have varying degrees of curvature in different embodiments. In an embodiment, device 103 may have a bendable structure. In an embodiment of the bendable structure, the device may be substantially continuously bendable. In another embodiment, the device may bend in bendable locations. For example, the device may have three sections and bend in the locations between sections. In another embodiment, there may be no curvature. The device may have a cavity 152 to house sensors, electronics, a battery and other components. In FIG. 6d, both sides of the device are shown connected to a belt 151. There are number of ways to connect the belt to the device. For example, there may be pass through slits in the device 157 to allow the belt 151 to pass through and connect back to itself as shown in FIG. 6e. The belt 151 may connect back to itself using, for example, magnets, clips, snaps, Velcro, or some other fastener. The device 103 may also connect to a strap 155 and the strap 155 may connect to the belt. The strap may be made from a bendable and soft material, or it may be made from a hard material like plastic. Alternatively, it may be made out of a combination of materials. For example, the device 103 may snap into a plastic element that is overmolded by a rubber or other bendable material. Many combinations are possible and may be utilized to meet the requirements of different applications.

Referring to FIGS. 7a-7c, an embodiment of the device utilizing EMG for the core sensor is shown. Since a potential difference between two nodes may be measured, two conductive ports Node A 161 and Node B 163 may be utilized. A top view of an embodiment shown in FIG. 7b shows Node A 161 and Node B 163 as conductive ports embedded in the surface of the device 103. An embodiment shown in FIG. 7c shows Node A 161 and Node B 163 as bumpers extruding from the face of the device. In an embodiment, the bumpers are fully conductive. In another embodiment, the bumpers are partially conductive. For example, the bumpers may be conductive at or near the tips of the bumpers and these conductive tips may connect to a conductive section that may connect to electronics within the device. An example of bumpers with conductive tips attached to a conductive center 164 are shown in FIG. 7c.

Referring to FIGS. 8a-8c, an embodiment of the device 103 utilizing backscattering for the core sensor is shown. Backscattering utilizes at least one transmitter 165 and at least one receiver 167. Both are shown as independent ports 165, 167 in FIGS. 8a-8b. It is shown as a single port 153 in FIG. 8c, with both transmitter and receiver combined in a single bumper. The transmitter signal may be audible, for example ultrasound; light, for example infrared; radio frequency or RF; or some other readily creatable signal that may backscatter differently when core muscles are relaxed and contracted. The design of the bumpers may be optimized for the nature of the signals being used.

Figure 9:
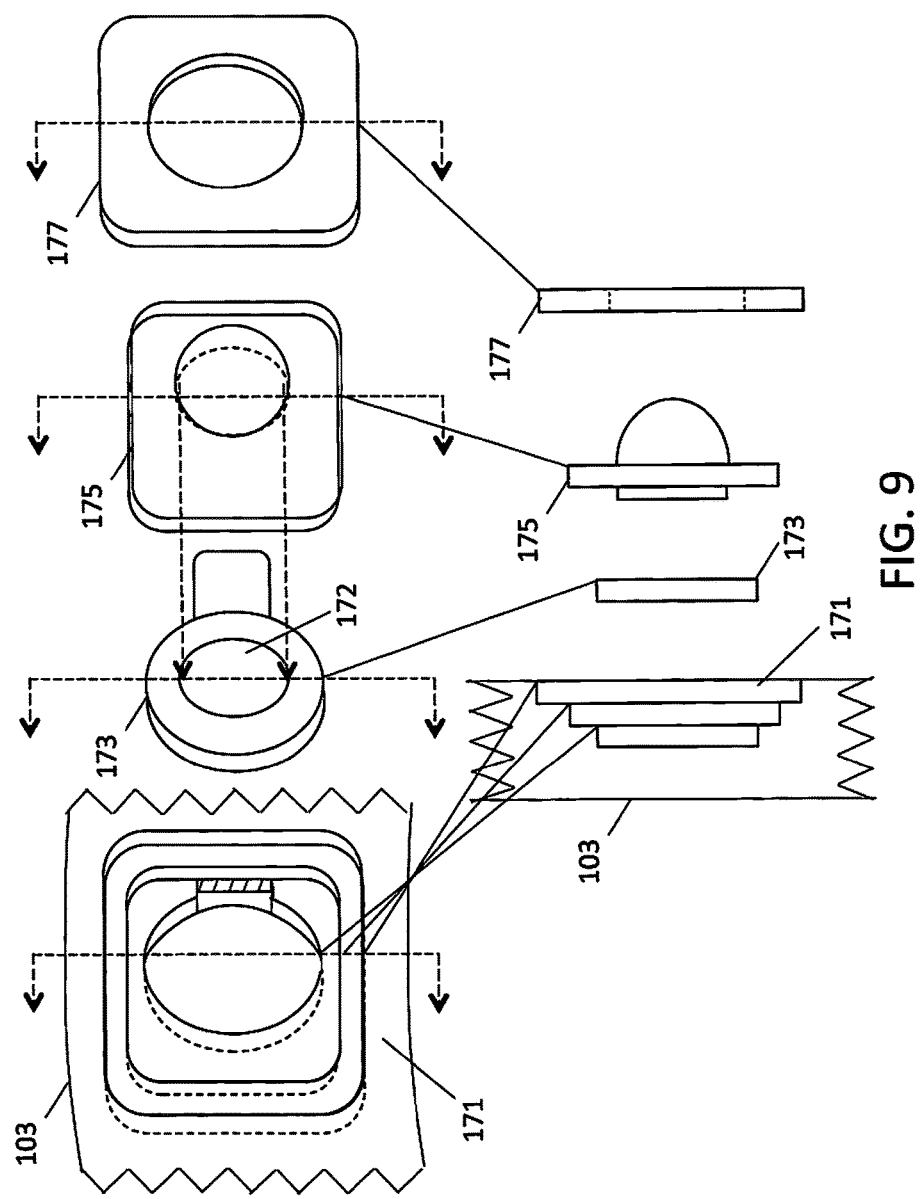
FIG. 9 illustrates an exploded view and a cross-sectional view of an embodiment of a core contraction sensor assembly.

Referring to FIG. 9, an exploded view of an embodiment utilizing an FSR 173 is shown on the top of the figure while a cross-sectional view is shown at the bottom of the figure. Starting at the upper left and moving to the right, the exploded view includes the device 103 with volume removed 171 to custom fit a force sensing resistor 173 with active area 172, a bumper 175 that may be implemented with a rubber or rubber-like material with a brim, and a frame 177 that holds the force sensing resistor or FSR 173 and bumper 175 in place by holding the brim in place. The frame 177 may be attached to the device using glue or one or more screws or other attachment materials. Additional features may be designed into the brim of the bumper including an O-ring in order to promote water resistance in the design. In the cross-sectional view, the deepest cavity is where the FSR 173 may reside. Above the cavity for the FSR 173 is a cavity where the brim of the bumper 175 may reside. Above the bumper brim is a cavity to fit the frame 177. Note in the cross-sectional view that the bumper 175 may have a small extrusion underneath it to interface to the active portion of the FSR 173. In an embodiment, the feature of the bumper 175 that interfaces to the user's 103 core may be shaped to achieve the objectives of comfort and sensitivity. In the example shown, the section of the bumper that will interface to the user's 101 core is shown to be rounded. In an embodiment, the bumper may have a substantially flat area on the tip that interfaces to the user's 101 core muscles while having a rounded top rim.

Figure 10B:
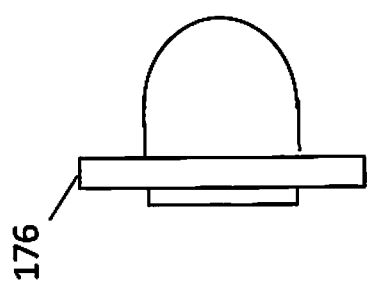
FIG. 10b illustrates an embodiment of a bumper with a second height.
Figure 10A:
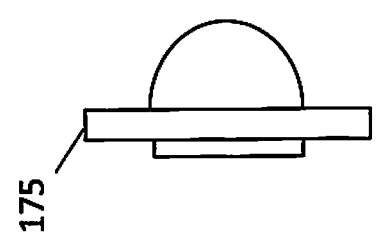
FIG. 10a illustrates an embodiment of a bumper with a first height.

Referring to FIG. 10, an embodiment may have bumpers with differing height to accommodate the body types of different users. A user with more body fat may benefit from a longer or taller bumper 176 as shown in FIG. 10b compared with the shorter bumper 175 shown in FIG. 10a.

Referring to FIG. 11a, an embodiment of an extender cap 181 which may be added to the top of the bumper 175 to further extend the effective height of the bumper 175. In FIG. 11b, an angled view is shown to further illustrate the extender cap 181 design to extend the effective height of the bumper. A side view of the cap 181 sitting on the bumper 175 is shown in FIG. 11c. In an embodiment, different sized caps 181 may be used to provide further variability in order to achieve greater measurement sensitivity while maintaining user 101 comfort. Different techniques may be used to attach a cap to the bumper. For example, the cap 181 may be sized to snuggly fit over the bumper 175 requiring no additional material or elements. Adhesive or double stick tape may be used to connect the cap 181 to the bumper 175. An additional extrusion may be designed into the bottom of the cap 181 to fit into an additional cavity in the bumper 175 as shown in FIG. 11d to provide additional stability for the combined structure including the cap 181 and bumper 175 as shown in FIG. 11e.

Figure 12A:
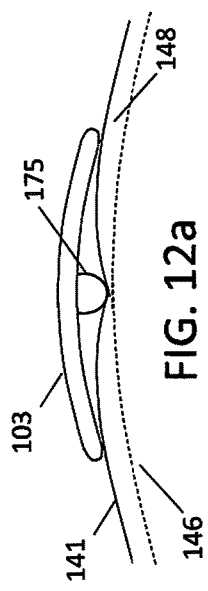
FIG. 12a illustrates a cross sectional view of an embodiment of the device and bumper placed on the core section showing the user's skin and underlying core muscles for a user with less body fat.
Figure 12B:
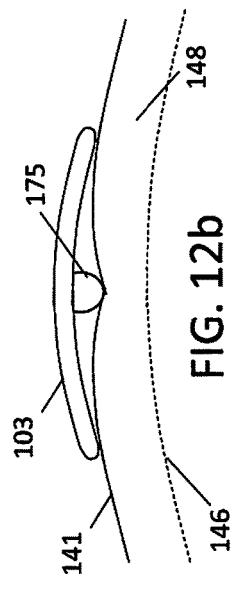
FIG. 12b illustrates a cross sectional view of an embodiment of the device and bumper placed on the core section showing the user's skin and underlying core muscles for a user with more body fat.
Figure 12C:
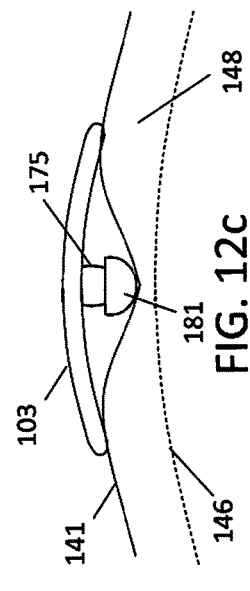
FIG. 12c illustrates a cross sectional view of an embodiment of the device and bumper with an extender cap placed on the core section showing the user's skin and underlying core muscles for a user with more body fat.

A device 103 with a small sized bumper 175 is shown in FIGS. 12a and 12b. In FIG. 12a, a depiction of a user 103 with less body fat 148 is shown and in FIG. 12b, a depiction of a user 103 with more body fat 148 is shown. In FIG. 12a, the bumper 175 is near the core muscles whereas the bumper 175 is shown to be far from the core muscles in FIG. 12b. In FIG. 12c, a taller bumper 175 with a cap 181 is shown with the depiction of the user 103 with more body fat 148. Note that the larger bumper 175 and additional cap 181 enables the sensor interface 153 to reach deeper and nearer to the core muscles.

Referring to FIG. 13a, a condition is shown where a user 103 with a small amount of body fat 148 also has prominent hip bones 154. When the belt 151 is used to hold the device 103 near the body, the belt 151 rests on the hip bones 154 which keeps the device 103 a distance away from the core so the bumper 175 is not able to properly contact the target core sensing area 145. Referring to FIG. 13b, a conceptual solution is proposed. With belt 151 effectively sitting on the prominent hip bones 154, conceptual adjoining line 55 connects the right and left side belt segments. Conceptually, the inventive solution enables the device 103 to move away from the adjoining line 55 and toward the body as indicated by the arrows 57. Using this approach, the gap between the adjoining line 55 and the target core sensing area 145 may be filled. In FIG. 13c, a strap 155 is introduced to continue the adjoining line between the belt segments and the device is attached to the strap 155 via connecting structures referred to as gap extenders 158. Introduction of the strap 155 and gap extenders 158 enables a gap filler 159 to be added between the device 103 and strap 155, which has the effect of pushing the device 103 and subsequently, the bumper 175 toward the user's 101 core muscles as shown in FIG. 13d. The gap filler 159 may be made of different types of material, depending on the design choices of the other components. For example, the gap filler 159 may be made of rubber or plastic or an additional appropriate material or materials. The gap filler 159 may be attached using connectors such as clips, Velcro, magnets, snaps, or other attachment techniques such as tongue-in-groove structures.

An embodiment showing all connections of the inventive device packaging is shown from top view in FIG. 14a and shown from the front in FIG. 14b. Slits 167 are cut out of strap 155 to allow the belt 151 to loop through the slits 167 and connect back to itself. It may be sewed to itself, connected by Velcro, or attached by a number of other attachment methods. Slits 167 may be seen in FIG. 14b, while the looping back of the belt to connect to itself is shown in FIG. 14a. The gap extender 158 may be a thin, light, and bendable material which starting from the left side may be attached 161 to the strap 155, pass through slit 157 in the device, pass around between the device 103 and the strap 155, then back through the slit 157 on the right side, and attach on the right side to the strap 155 at location 161 on the right side of the device shown in FIG. 14b. In an embodiment, a very thin material is used for the gap extender 158 to minimize its contribution to thickness between the device 103 and strap 155, and to keep it from keeping the ends of device 103 from contacting the user's 101 core section. In FIG. 14b, the connecting structure 158 is drawn for illustrative purposes thicker than may be desired. In an embodiment, the gap extender 158 may be elastic or partially elastic. In an embodiment, the gap extender 158 may be made of the same or similar material to the strap 155.

In applications where the bumper makes direct contact to a user's 101 skin or to certain materials of clothing, the bumper may stick or grab on to the user's 101 skin or clothing for some angles and amounts of pressure. Referring to FIGS. 14c and 14d, a soft buffer material 162 resistant to sticking or grabbing may be placed over the location where the bumper couples to the user's 101 core muscles. In an embodiment, the stick resistant buffer material 162 may be cotton, polyester, nylon, microfiber or other material, or may be made from a blend of different types of materials. A number of materials are being used and developed for high performance athletic apparel. These materials may be appropriate for stick resistant buffer material. In an embodiment, the stick resistant buffer material 162 may be a type or combinations of types of rubber. In an embodiment, buffer material 162 may be manufactured into the bumper 175 via a surface layer that may be resistant to sticking or grabbing.

Several implementations may be used to hold the buffer material in place. For example, the buffer material 162 may be designed into a tubular shape that slips over the device 103 or portions of or all of the strap 155 which may include the gap extender 158. FIG. 14c shows an example of a tubular shape forming a stick resistant sock 162 to the right of the wearable 103 before it is slipped over the device 103. FIG. 14d shows the stick resistant sock 162 in position over the bumper. In an embodiment, the buffer material 162 may be made from a stretchable material, allowing it to stretch to accommodate different bumper heights. In another embodiment, the buffer material may be made from a material or materials with water resistant qualities. In an embodiment, the stick resistant sock 162 may be made from a material or materials with water resistant qualities, and designed to fit snuggly on both ends over the wearable device 103 as shown in FIG. 14d. The snug fit on the ends of sock 162 may be implemented in a number of ways. An embodiment may utilize a material that stretches. Making the entire sock 162 with stretchable material and designing said sock to fit snuggly may result in snug ends when the sock 162 is on the device 103 and the stretchable material may stretch over the bumper to accommodate different bumper heights. Another embodiment may utilize elastic or a material with qualities of elastic that are sewn in or attached to the ends of the sock. Another embodiment may utilize rubber or a material with qualities of soft bendable rubber that may be molded to fit over the device 103, fit snugly on the ends, and have a stretchable area over the bumper or designed with extra volume to accommodate different bumper heights. By combining a design in which all openings to the cavities of the device fit within or under the coverage of the stick resistant sock 162, and making the sock 162 from a material or materials with water resistant qualities with a snug fit on the ends, the combined structure including the device and stick resistant sock 162 may be substantially splash proof from water or other liquids including a user's 101 perspiration. In said design, the strap 155 may have design features to support keeping the sock 162 in position over the device. In an embodiment, the stick resistant sock 162 may be made from a low-cost water resistant material and be designed for a limited number uses and be disposable for certain applications. For example, after using the wearable device with a user 101 during a therapy session, the therapist 107 may remove a limited use and disposable stick resistant sock 162 and put on a new sock 162 for a next user 101.

Figure 14E:
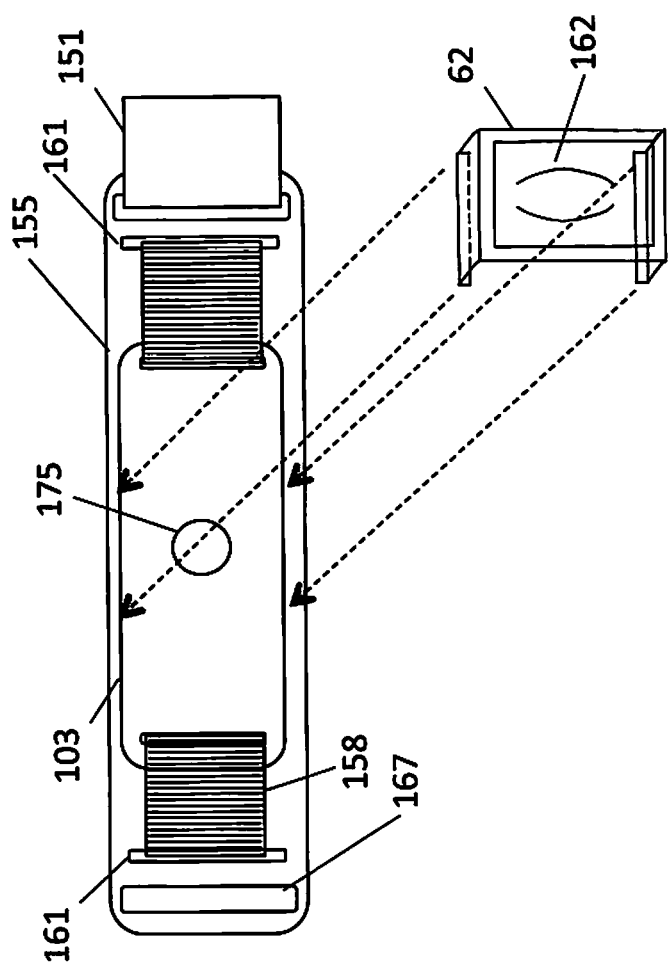
FIG. 14e illustrates an additional element that may snap or clamp onto the face of the device in order to hold material over the bumper.

In other embodiments, the buffer material 162 may be fitted onto an additional element 62 that may snap or clamp on over the face of the device, allowing the bumper 175 to be covered by the buffer material 162 as shown in FIG. 14e. Element 62 may be made out of metal, plastic, or other firm and bendable material. Buffer material 162 may be attached to element 62 using glue, thread (sewed on), or other attachment techniques or materials. In these embodiments, use of water resistant materials for the buffer material 162 and appropriate placement of the element 62 over the device openings may combine to result in a splash resistant wearable device 103. Openings into the device may include an opening to place the PCB, battery, and sensors which may be covered with a fitted cover and held in place by one or more screws, glue, or other attachment devices or materials; ports for battery charging; a communications interface connector which may additionally support battery charging such as USB; and a sensor interface port as described with reference to FIG. 9 which may be covered by a frame and held in place by one or more screws, glue, or other attachment devices or materials.

The inventive sock 162 is an example of a buffer that may be used between the bumper and the user's 101 core. Design elements of the buffer as described may be applied to other implementations to achieve similar objectives. A summary of key design element of the inventive sock 162 may include: a. provides stick or grab resistance between the bumper and the user's 101 skin or clothing; b. with appropriate design of the sock 162 and device 103, the combination may be splash proof; furthermore, the strap 155 and gap extender 158 may be designed to support maintaining the sock 162 in position over the device; c. accommodates different bumper heights or may be designed to fit certain ranges of bumper heights; d. can be made with relatively low material and manufacturing cost and using plastic wrap or thin rubber material may be made disposable; e. may be made from materials used in high performance athletic apparel and may be washed and re-used; and f. simple to remove and replace so may be used by a therapist for multiple users and a new or clean sock 162 may be put on for the start of each user 101 session.

To summarize, the presented modifications in the wearable device are examples of the way the wearable may be modified to achieve high sensitivity to identify core contractions while being comfortable for a user 101 and allow a user to comfortably wear the device 103 for long periods of time. To address different amounts of body fat 148 on a user 101 and differing degrees of muscle fitness of a user, variable bumper 175 heights and additional structures such as extender caps 181 may be employed. More generally, a cap 181 may be any additional structure added to increase height or bring a preferred or more comfortable shape to a bumper 175. In an embodiment, the cap 181 does not substantially increase the height of the bumper 175 but instead adds width to the bumper 175 which may make it more comfortable for a user 101. To address the case of prominent hip bones 154, a strap 155 may be used in combination with a gap extender 158 that allows the provision for additional gap filler structure 159 to be added between the strap 155 and the device 103. Variable belt 151 thicknesses may also be used, particularly on the portion of the belt 151 that wraps around a user's backside which may improve wearability and comfort. In an embodiment, instead of using a shorter bumper, an additional face plate may be attached to the face of the device 103 so that the height of the bumper 175 coming out of the face of the device 103 is effectively reduced. In order to reduce the possibility of the bumper sticking to the user's 101 skin or clothing, a buffer material 162 may be attached to the wearable 103 to cover the bumper 175 to resist sticking. These modifications may be used in isolation or in combination. Other modifications may be utilized to achieve the objectives. In an embodiment, all the materials except the device 103 may be separated from the device 103 and put into a standard washing machine for washing. In an embodiment, the materials may be selected to allow a washed strap 155 and belt 151 to be quickly towel dried. In an embodiment, the materials may be hypoallergenic, minimizing allergic reactions due to regular contact with a user's 101 skin.

Figure 15C:
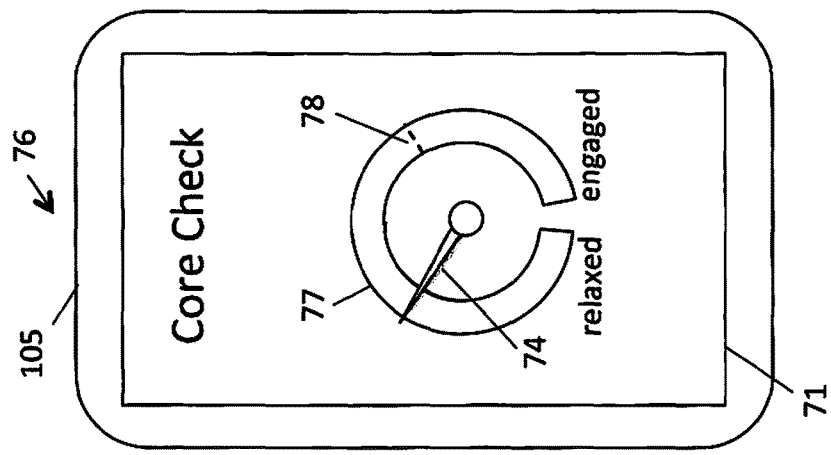
FIG. 15c illustrates a screen shot of an embodiment of the Core Check app to report the core sensor number using a dial.
Figure 15B:
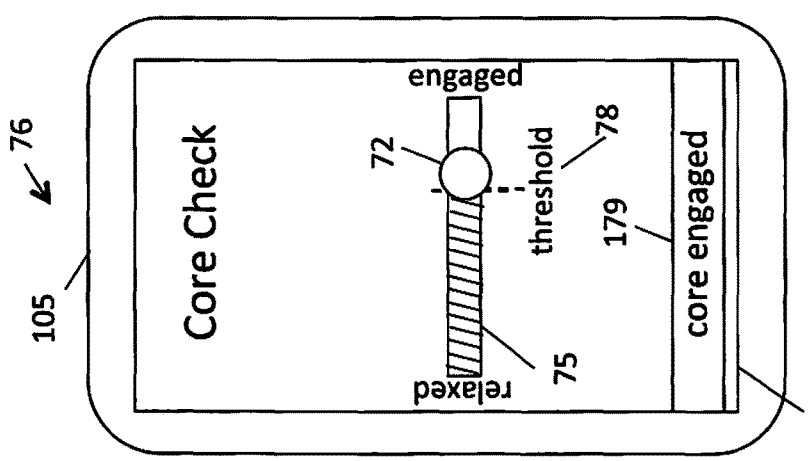
FIG. 15b illustrates a screen shot of an embodiment of the Core Check app to report the core sensor number using a slider and a core engaged indicator.
Figure 15A:
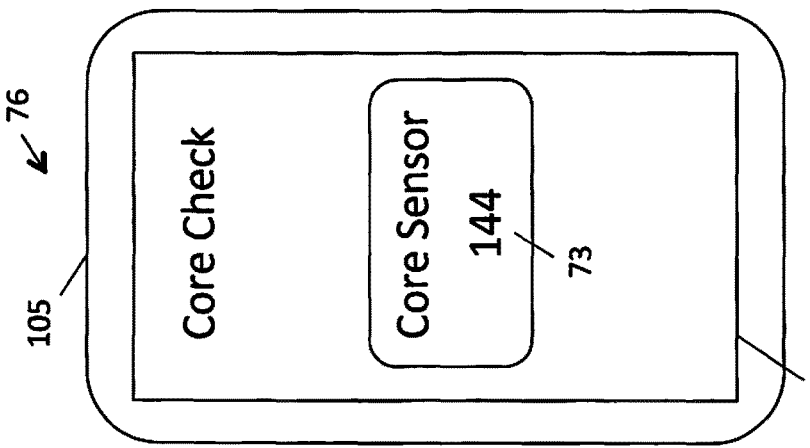
FIG. 15a illustrates a screen shot of an embodiment of the Core Check app to report the core sensor number.

The wearable device 103 may connect to a smart device such as a smart phone, smart pad, PC, or dedicated device running an app. The app may run on the iOS or android operating system, or it may run on a proprietary operating system. Referring to FIGS. 15a-15c, an embodiment where the app is run on a smart phone 105 is shown and illustrative content for the Core Check app 76 is shown on the display 171. The Core Check app 76 may be a portion of a more complex app. In this description, we will refer to the Core Check app 76 as an app running on a smart device 105 that may provide feedback data regarding the contraction state of a user's 101 core muscles. In an embodiment, one function in the Core Check app 76 may be to display a core sensor number 73 which is a number related to the core sensor measurement taken by the wearable device 103 regarding the status of the user's 101 core muscles. In the case where an FSR is used, the FSR may be connected between a voltage, for example the battery voltage and an output node. There may then be a resistor connecting the output node to ground. As one skilled in the art may understand, this configuration is an impedance divider. If the FSR has zero or little incident pressure, the FSR resistance is very high, for example 5 mega ohms and the output node may be near ground. As force is applied to the FSR, the resistance drops. As a result, the output node may increase in voltage. If the core is contracted using bracing, the force on the device may increase and the core sensor number 73 which may be the output voltage translated to a digital code between 0 and 255 in an 8-bit representation may also increase. The result is if the core is relaxed, the output code or core sensor number 73 may have a target value between, for example, 140 and 160. If the user braces to engage their core, the core sensor number 73 may increase to a number, for example, near 180. If the user hollows to engage their core, the core sensor number 73 may decrease to a number, for example, near 110.

There are a number of ways the core sensor number or core sensor value 73 may be communicated to the user 101 through the Core Check app 76. In FIG. 15a, the core sensor number 73 is provided simply as a number 73. In the instance shown, the core sensor number 73 is 144. In FIG. 15b, the core sensor number 73 is presented on an embodiment of a slider 175 where an element such as a circle 72 moves left to right on a rail. A low value of the core sensor number 73 corresponding to a low pressure on the core sensor in the wearable 103 may result in a movement of the circle 72 to the left. A high value of the core sensor number 73 corresponding to a high pressure on the core sensor in the wearable 103 may result in a movement of the circle 72 to the right. To further illustrate, let us consider example values. Suppose the minimum value to be displayed is 100 and the maximum value to be displayed is 200. A core sensor number 73 of 100 or less may place the movable circle 72 on the far left of the rail while a core sensor number 73 of 200 or more may place the movable circle 72 to the far right of the rail. The location of the circle for values between 100 and 200 may be substantially linear. In this example, suppose that the user has selected bracing (as opposed to hollowing), the target range for a relaxed core is set between 140 and 160, and the threshold value 78 for identifying a core contraction is 170. Suppose the user 101 contracts their core and core sensor number 73 is 175, circle 72 is to the right of threshold 78 and a contracted or engaged core may be identified by a core engaged indicator 179.

In FIG. 15c, the core sensor number 73 is presented in the form of a dial. In an embodiment, as the core sensor number 73 increases, rotating pin 74 rotates clockwise. When the pin 74 points to the right of threshold 78, the core may be determined to be contracted. If it points to the left of threshold 78, the core may be determined to be relaxed. These examples illustrate principles and capability of the Core Check app 76 to provide real-time data regarding the status of the core of the user 101 and their therapist, doctor, teacher, trainer or coach 107 in different formats. In some applications, other formats may be preferred. In some embodiments, one or more output formats for reporting the core sensor number or core sensor value 73 may be used simultaneously.

The data provided for core sensor numbers 73 provided in the example just described with FIG. 15 are used for the purpose of illustrating an embodiment of the system. In the example presented, bracing was assumed for the core contraction approach and simple thresholding was used to identify a contracted core where a fixed threshold value 78 was selected. If the core sensor number 73 is greater than or equal to the threshold 78, the core may be identified to be contracted. If the core sensor number 73 is lower than the threshold 78, the core may be identified to be relaxed. Another approach described in U.S. Provisional Application No. 62/027,409 may be referred to as Relaxed Core Tracking Threshold. This algorithm for identifying a core contraction is not referred directly by this name in said patent application, but is described with reference to FIGS. 21a-21d in said patent application. In this approach, the core contraction sensor number or output 73 is tracked by a low-frequency tracking block when the core is relaxed and a threshold is added to the output of this tracking block. This is called the relaxed core tracking threshold because this threshold tracks the low-frequency tracking block output. This algorithm tracks slow changes in the core sensor number 73 as a user 101 performs movements with their core relaxed. In one embodiment, the low-frequency tracking block may be a low pass filter operating on the core sensor number 73 data when the core is determined to be relaxed. When the core sensor number 73 equals or exceeds the relaxed core tracking threshold, the core is determined to be contracted. When the core sensor number 73 is less than the tracking threshold, the core is determined to be relaxed. In principle, a smaller change in core sensor number may be required to be identified as a contracted core when using the Relaxed Core Tracking Threshold compared with simple thresholding. This makes contracting the core to a degree firm enough to be identified as a contracted core easier for a user 101 when Relaxed Core Tracking Threshold is used compared to when simple thresholding is used. For example, suppose a threshold of 10 units is used with Relaxed Core Tracking Threshold with a relaxed target range between 140 and 160. If the short term average core sensor number is 140 and a threshold of 10 units is used, the core sensor number 73 would need to change by 11 units to 151 as the core transitions from relaxed to contracted in order to be identified as a contracted core. Conversely, if simple thresholding is used, if the relaxed target range is between 140 and 160, the minimum threshold would be 170 in order to be 10 units away from 160. If the core sensor number for a relaxed core is 140, the core sensor number 73 will have to increase 31 units to 171 to be identified as a core contraction. Such a large change in the core sensor number transitioning from relaxed to contracted may be difficult to consistently attain. As a result, Relaxed Core Tracking Threshold may result in a preferred behavior by the core contraction identification algorithm compared with simple thresholding. As belt 151 tightness changes as a user 101 moves and as belt tightness varies due to such movements, an algorithm based on simple thresholding with a fixed threshold 78 may have performance limitations and result in more missed positive core contraction identifications or more wrongly identified core contraction identifications than an algorithm based on Relaxed Core Tracking Threshold.

An example of an issue that the relaxed core tracking threshold approach may encounter that simple thresholding may not encounter will be described. When a user 101 adjusts the device 103 with the belt 151 around their waist, they may pull the device away from the body by a small amount, for example one or two inches, and then release the device 103 in order to put the device in place and straighten the belt 151. A transient step may be seen in the core sensor number 73 when the device 103 impacts the user's 101 body, which may be identified as a core contraction by the relaxed core tracking threshold algorithm. Since the user's 101 core may actually be in the relaxed state at this instant, the device 103 may continue with a contracted core identification. In other words, the system may be stuck undesirably in a contracted core identification state: the user's 101 core may be relaxed, yet the device may identify a contracted core. This condition may continue indefinitely without an intervention. In an embodiment, the system may include such an intervention for this condition. A provision may be included in the algorithm to allow the user 101 to perform an action that may be identifiable by the device 103. When the action is identified, the device 103 may reset and identify the current core sensor number 73 as a relaxed core. In an embodiment, when the user 101 identifies the device or system being stuck incorrectly in a contracted core identification state, the user 101 may tap on the device 103 or push on the device 103. The action of a tap on the device 103 may be detected as a transient by the movement sensors or the action of a push on the device 103 may be detected as a large positive transient in the core sensor number 73. The detected tap or push may be identified by the processor as a core sensor algorithm reset, and the algorithm may interpret the core sensor numbers following the tap or push as a relaxed core condition. This intervention may transition the system from being stuck in an incorrect core contraction identification state to the correct relaxed core identification state. In an embodiment, the movement sensors may be programmed to identify two or more taps or a tap pattern as a signal to reset the core sensor algorithm out of an incorrect core contraction identification condition.

Another limitation of the relaxed core tracking threshold algorithm will be described. Certain body movements may result in large variations in incident pressure on the wearable device 103 due to the change in orientation and pressure against the body. For example, as a user 101 moves from a kneeling position to a standing position the core sensor number 73 may change considerably due to the way the device 103 presses against the core muscles in both positions. Use of movement data derived from the movement sensors may be combined through characterization and calibration techniques to improve core contraction identification over more conditions of body positioning including for example, the position change from kneeling to standing.

Figure 16:
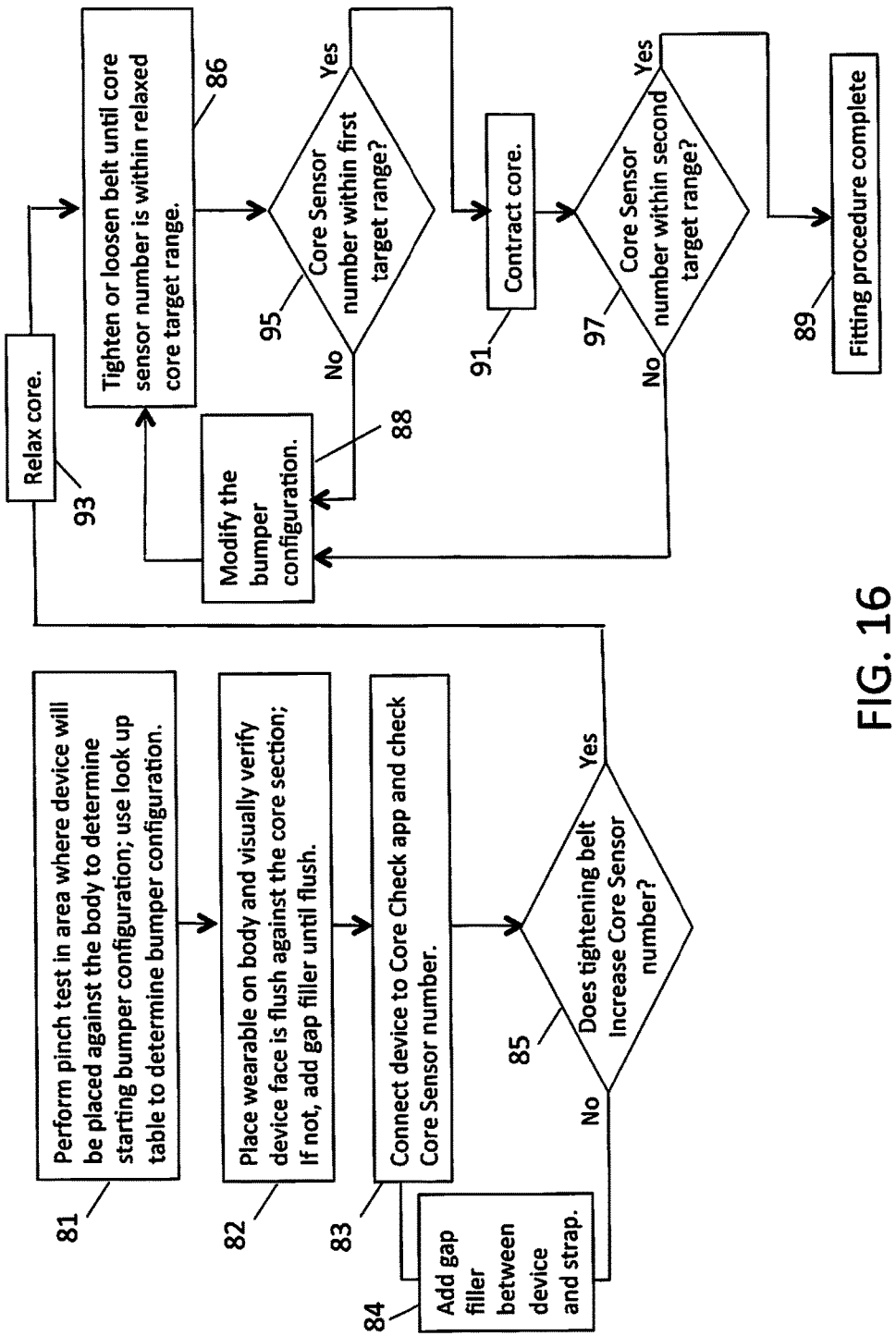
FIG. 16 illustrates an embodiment of a flow chart for fitting a wearable device to a user.

It is important that the wearable device 103 be properly fitted to each user 101. The fitting process may be iterative. It may be desirable for a user 101 to minimize the number of iterations needed to properly fit a wearable 103. A properly fitted wearable 103 may meet fitting criteria that may include: a. it is comfortable to wear and can be comfortably worn for long periods of time; b. the core contraction sensor may correctly detect a relaxed core; c. the core contraction sensor may correctly detect a contracted or engaged core; and d. the movement sensors may correctly detect qualifying movements. Referring to the flow chart in FIG. 16, let us assume an implementation of a system using an FSR as the core sensor and the strap 155 structure described with FIG. 14. The fitting process may be modified appropriately if a different technology for the core sensor is utilized and may also be dependent on the core sensor interface 153 utilized. It is desirable to start with a good estimate of the appropriate bumper 175 configuration. This may be determined as follows starting with a pinch test. Perform pinch test in area where device will be placed against the body to determine starting bumper configuration; use look up table to determine bumper configuration 81. In the area where the bumper 175 will contact the body, above, near, or below the belt line 145, gently pinch the skin and grab as much of the body fat that is available.

A table look-up process may then be used. The number of elements of the table used for the table look-up may depend on the number of available bumper 175 configurations. If the amount pinched is less than a certain thickness, then one bumper configuration 175 may be appropriate. If the amount pinched is greater than a certain thicknesss but less than another thickness, a second bumper configuration 175 may be more appropriate. When larger amounts of skin and fat are pinched, a larger bumper configuration 175 may be appropriate. The larger bumper configurations 175 may include extender caps 181. Each available bumper configuration may be associated with a width of skin and fat pinched during the pinch test. This process may yield a good starting point for the bumper configuration 175. Next, Place wearable on body and visually verify device face is flush against the core section. If not, add gap filler until flush 82. Place the device 103 on the body with the core sensor interface 175 on the preferred target core sensing area 145. Perform a visual check to see if the face of the device 103 is flush against the core area 145. If it is not, find the gap filler 159 with the smallest available thickness until the face of the device 103 is flush against the core sensing area 145. This may require repeated tries until the appropriate gap filler 159 is identified.

Connect device to Core Check app and core sensor number 83. Connect the wearable device 103 to a smart device 105 running the described app, and open the Core Check app 76. At this point, tightening the belt 151 should result in a higher reading of the core sensor number 73 and loosening the belt 151 should result in a lower reading of the core sensor number 73. Does tightening belt increase core sensor number 85? If the core sensor number 73 is not increasing with a tighter belt 151, then add a gap filler between device and strap 84 may be performed or a thicker gap filler 159 may be needed if one is already in place. Once the initial bumper 175 configuration is set and gap filler 159 is added (if needed), move on to the next step.

Relax core 93. Adjust the belt 151 tension to a firm but comfortable level on the waist. The belt 151 should not be too tight or too loose. Tighten or loosen belt until core sensor number is within relaxed core target range 86. Once a comfortable belt 151 tightness is obtained, check the core sensor number 73 on the Core Check app 76. Is the Core Sensor number within first target range 95? Using the example started in the description referring to FIG. 15, the target range of the core sensor number 73 with a relaxed core may differ depending on many factors. In an embodiment, the first target range may be different, depending on the experience level of the user 101 with using their core muscles and the algorithm used for identifying a core contraction. This process may also factor in an individual's preferences and comfort as well and a core sensor number 73 in the relaxed core condition outside the target range may be acceptable. The wearable 103 must be comfortable for the user 101 to encourage a high degree of usage. If the core sensor number 73 is outside the target range and the user prefers to have the core sensor number 73 within the target range, the user 101 may modify bumper configuration 88. If the core sensor number 73 is above the target range, the bumper configuration 175 may be lowered in height. If the core sensor number 73 is below the target range, the bumper configuration 175 may be increased in height. At this point, the wearable 103 should meet the fitting criteria of being comfortable, and the core sensor number 73 when the core is relaxed should be within the first target range for a relaxed core. Contract core 91 and again check Core Sensor number 73 within second target range 97? If it is not, return to Modify bumper configuration 88. If the core sensor number 73 is within the second target range of a contracted core or meets any modifications to the algorithm for identifying a contracted core, Fitting procedure complete 89 is attained.

In an embodiment, the second target range may be defined differently when simple thresholding or Relaxed Core Tracking Threshold is used to identify a core contraction. Let us consider an example where a minimum change of 10 units when transitioning from a relaxed to a contracted core is to be identified. In an embodiment using simple thresholding, a fixed value greater than the first target range may be used. For example if the first target range is 140 to 160, the second target range may be any value greater than or equal 170 when simple thresholding is used. In an embodiment using Relaxed Core Tracking Threshold, the second target range may be a threshold value added to the short term average of the relaxed core value. For example if the first target value range is 140 to 160 and the actual short term average of the relaxed core value is 153 and a threshold value of 10 is used, the second target range may be any value greater than or equal 153 plus 10 or 163.

If after several iterations, the core sensor number 73 when the user's 101 core is engaged as measured by the Core Check app 76 do not meet the target values, there may be more than one reason. First, the core engagement may not be performed properly. It is desirable that a user 101 work with a therapist or coach 107 to verify proper core engagement. Second, the wearable device 103 may not be configured properly or may be out of the range of available sizes. For example, a larger bumper configuration 175 may be needed. The user 101 may work with their therapist or coach 107 to have them help with the fitting process.

In an embodiment, the wearable device 103 may be programmed by the smart device 105 to be placed into the mode where the device may provide Core Contraction Feedback 116 to the user 101. The smart device 105 may also enable settings and parameters for the core contraction tracking algorithms to be selected or modified. Examples of such settings may include the decision threshold and tracking filter bandwidth. In an embodiment, feedback may be provided in the form of a buzz or a pattern of buzzes by a buzzer on the wearable device 103. In an embodiment, the feedback buzz or pattern of buzzes may have a duration that is substantially similar to the duration of time that the core is determined to be contracted by the core contraction sensor and processor on the wearable device 103. In an embodiment, the buzz pattern may be programmable and have features that are customizable by the user. For example, features that may be customized may include placing buzzes of different duration such as short, medium, and long in different sequences and repeating the sequences with user programmable time periods. For example, a short buzz duration may be 100 msec, a medium buzz duration may be 200 msec, and a long buzz duration may be 400 msec. In another embodiment, a buzz sequence may be utilized, comprised of different buzz patterns. For example, a first buzz pattern may be used at the start of the core contraction, a second buzz pattern after the start and until the end of the core contraction, and a third buzz pattern after the end of the core contraction. For example the first buzz pattern may be two short buzzes, the second buzz pattern may be silent, and the third buzz pattern may be a single long buzz. Many buzz combinations are possible and may extend into the time when the core contraction is determined to be complete. Buzzing is one of many possible output signals that may be emitted by the wearable device 103. Similar variations in output patterns may be used with different output signal sources. In another embodiment, data may be provided by the core contraction sensor to a processor on the smart device 105 or companion device, and the processor on the smart device 105 or companion device may communicate to the wearable device when and what feedback signal to output. In an embodiment, this feedback signal may be in the form of a buzz, pattern of buzzes, or sequence of buzzes. In another embodiment, the feedback signal may utilize sound generation and synthesis capabilities of the smart device 105 or companion device and have programmable features and parameters that may be selectable by the user 101. In another embodiment, the feedback signal may utilize another output signal generating technology other than buzzing and sound and have programmable features and parameters that may be user selectable.

Isolated core contractions are a way for a user 101 to focus on identifying and contracting the core muscles. Isolated core contractions may be performed while the user 101 is standing or sitting and in the absence of any other movement. Some therapists may prefer that patients hollow their abdomen when contracting their core. Hollowing may be associated with a pulling the navel inwards toward the spine. Use of the slider display 75 of the core sensor number 73 in the Core Check app 76 may allow the movement of the target region of the core to be tracked and displayed. As the user 101 contracts or engages their core muscles during isolated core contractions, the user 101 may receive core contraction feedback 116 in different forms. For example, the user 101 may receive feedback through the app as described with in FIGS. 15*a*-15*c*. In an embodiment, audible feedback may be generated by the smart device 105 while the core is identified to be contracted. In another embodiment, the wearable 103 may be programmed to buzz, provide a buzz pattern, or provide a buzz sequence when a core engagement is detected.

Therapists 107 may often utilize exercises on gym equipment as part of a therapy or training session. Utilizing the core to support the lumbosacral junction and lumbar spine 132 may be encouraged by the therapist 107 during the execution of the exercises. There are two use models that may be utilized with the inventive device and system as shown in FIG. 17. Referring to FIG. 17*a* the depiction of a user 101 performing an exercise often referred to as lat pull-downs is shown in time sequence moving left to right. There are two movements of the exercise as identified in the figure: pull-down 193 and release-up 195. Below the identified movements are examples of contraction of the user's 101 core indicated by the Core Status bars 197 shown in FIG. 17*b*. During the pull-down movement 193, the user's 101 core is contracted before, during, and after the movement as illustrated by the bar indicating core contraction 197 overlapping the duration of the movement 193. During the release-up movement 195, the user's 101 core is not contracted during the entire movement. Thus, while the pull-down movement 193 may be characterized as protected, the release-up movement 195 may be characterized as being not protected. Two use models Audible Core Tracking which is a form of core contraction feedback 116 and Movement and Core Sensing/Discriminating which is a form of qualifying movement feedback 119 will now be described.

When using Audible Core Tracking, the Core Check App 76 may be utilized with an audible option turned on. With this option, when the user's 101 core is contracted, there will be a sound from the smart device 105 as indicated by the hatched bar in Approach 1 in FIG. 17c. This sound may be used as a feedback to the user 101 and the therapist 107. Examples of the sound include cello, drum beat, or a song of the user's 101 choosing. Alternatively, an image signal may be shown on the smart device when the core is contracted. Examples of the image signal may be a flashing light or the words "Core Contracted". In another embodiment, the device 103 may be used in a device-only mode, and the device may buzz a specific buzz pattern when the core is detected to be contracted. When the device 103 provides feedback, the smart device 105 may not be required during the time the device-only mode is utilized since the smart device is not required to provide feedback. The device-only mode may be utilized in many applications where the system provides core contraction feedback 116. In an embodiment, the device 103 in device-only mode may also provide additional feedback when unfavorable movements are detected by the movement sensors such as the user 101 bending over at the hips to pick an object off the floor. In an embodiment, this additional feedback may be provided in the form of a specific buzz, sequence of buzzes, or buzz pattern.

When using Movement and Core Sensing/Discriminating, the companion device described in U.S. Provisional Patent Application No. 62/025,929 may be utilized. The Companion Device 192 is shown attached to the weight stack in FIG. 17a. As shown in Approach 2 in FIG. 17d, during the pull-down movement, the companion device 192 has a move-up movement 201, and during the release-up movement, the companion device 192 has a move-down movement 203. As described in the aforementioned patent application, sensor data from the companion device identifies a Qualifying Movement while the wearable device determines when the core is contracted. The core contraction is tested against the Qualifying Movement duration by the discriminator function implemented in the algorithms running on the microprocessor in one of the devices or an accompanying smart device 105. The pull-down movement 193 is shown as a protected movement so there may be no Feedback-Buzz during the pull-down movement as shown in FIG. 17e. However, the release-up movement 195 is not protected, and there may be a Feedback-Buzz after the release-up movement 195 as indicated in the figure. In addition to this feedback that may be provided during each repetition of an exercise, the wearable device 103 and system may also store data to report a Core Score.

As described in the said previously filed patent applications and provisional patent applications, the Core Score is a quantifiable measure of the number of protected movements to the number of Qualifying Movements. For example, the Core Score may be reported as the number of protected movements divided by the number of Qualifying Movements. This number may be reported in different formats. For example, if 30 protected movements are detected out of 40 Qualifying Movements, the core score may be reported as 30/40, 0.75, 75, 75%, or 750 where 750 is obtained by multiplying 30/40 by 1000. The Core Score may be reported over different periods of time as specified by the user 101. The Core Score data memory may be reset to zero via a button on an app. A record of each protected movement and each Qualifying Movement may be stored in data memory with a time stamp. The user may then request the reporting of a Core Score over a specific period of time. For example, the Core Score may be reported since 6:00 am this morning, or all of yesterday, or over the past 7 days. The Core Score over the course of a day may be texted or emailed to the user 101 and the user's therapist 107. In addition, users may compete with friends, colleagues, or others on a regular basis to have the highest Core Score over the same or similar period of time.

Short animated tutorials or exercise apps 66 may be available as a part of the app that runs on a smart phone or smart device or PC 105. One such example is shown in FIGS. 18a-18c, depicting a person 102 performing simple practice movements of sit-to-stand. In FIG. 18a, the FIG. 102 is shown seated and with no core contraction. In FIG. 18b, the FIG. 102 is shown contracting their core muscles 215. Then in FIG. 18c, the FIG. 102 is shown still contracting their core muscles 215 while in the process of standing up. In the full app exercise, the FIG. 102 will alternate between performing the stand-to-sit movement and the sit-to-stand movement. One objective of such practice movements is to have the user 101 practice contracting their core just before and during the movements. And in many applications, to relax their core between movements. The wearable device 103 may track a movement performed with the animation, identify the start and end of the movement, and compare the relative timing of the contraction of the core to determine whether or not the movement is protected. If it is not protected, the user 101 may select a buzz option through the exercise app 66 (not shown as an icon on the app) in which case the wearable 103 will perform an electronic buzz. In an embodiment, the buzz button may toggle on and off through touch control by the user 101 through the exercise app 66. In an embodiment, the number of repetitions or reps 217 of the exercise may be changed and tracked by the user 101 through the exercise app 66. In an embodiment, the duration of one repetition may be changed by the user 101 through the exercise app 66.

Practice apps may operate in many modes and feedback may be provided to the user in different ways. Two such ways are mirror 21 and follow 23 as shown in FIG. 19. In mirror mode 21 shown in FIG. 19b, the system assumes the start and stop of the Qualifying Movement is defined by the movements of FIG. 102 in the practice app video. It is this time definition of the QM that is used with the timing of the core contraction 225 detected by the wearable device to determine whether the QM is protected or not protected. In other words, the system assumes the user is accurately or somewhat accurately mirroring the timing of the FIG. 102 in the exercise app. In follow mode 23, the system assumes the user 101 is following the movements of the FIG. 102 in the practice app, but not necessarily at the exact same time. Instead, sensors in the wearable device are used to determine the start and end of a QM. This definition of the QM timing 227, 229 together with the core contraction 225 timing also identified by the wearable 103 is used in the determination of a protected or not protected QM.

An embodiment of a block diagram of the basic operating mode of the system as presented in U.S. patent application Ser. No. 14/132,808 is shown in FIG. 20a. The system monitors body movements and the core activity for core contractions 231. When a Qualifying Movement (QM) is identified 232, the core activity before and during the QM 232 may be compared with the duration of the QM. Based on the timing of the core contraction and the QM, the system may determine if the movement is Protected or Not Protected 234. It may then provide feedback 235 to the user 101.

In untethered mode, the wearable device 103 may operate without a smart phone 105 app. Since in this mode the wearable device 103 may operate independently, we refer to this mode as untethered. In this mode, the wearable device 103 may monitor body movements to identify Qualifying Movements and the core for core contractions. Each identified QM and the associated core status may be used to determine whether or not the QM is protected or unprotected. Data associated with each QM and whether or not it was protected along with a time stamp may be stored in memory on the wearable device. An example app we refer to as the Untethered App 96 may provide information as shown in FIGS. 20b-20c, the outcome of whether or not the QM is protected or not protected (unprotected) 239 may be reported by the exercise app 96. The last movement identified 238 may be provided by the untethered app 96. Furthermore, for the selected starting time to second selected time including the present, the Core Score 236 may be reported. All data may be calculated and stored on the wearable device and downloaded to the smart device 105 or PC at a later time. In an embodiment of untethered mode, the Smart Phone may be used only for data reporting.

One way of characterizing the In-Session 108 and Out-of-Session 109 use models is as shown in the table 241 of FIG. 21. In-Session 108, the device 103 and system may be used with Use No. 1 which is to provide feedback as the therapist 107 is teaching the user 101 to contract their core during isolated core contractions. Use No. 1 utilizes core contraction feedback 116. In an embodiment, the feedback may be provided by the device 103. Use No. 2 describes two models for using the device 103 and system during exercises. In Use No. 2a, the wearable device 103 tracks core contractions and may provide feedback through the device 103 or smart phone or smart device 105. Use No. 2a utilizes core contraction feedback 116. In an embodiment, the feedback may be provided by the device 103. In Use No. 2b, a companion device is used to track movement of the exercise equipment or may be attached to the user's 101 wrist to track movement of the user's 101 hands as described in the aforementioned patent and provisional patent applications. Use No. 2b utilizes qualifying movement feedback. Use No. 3 is the first Out-of-Session 109 use model in the table and includes interactive exercises that a user may be prescribed to do one or more times each day. Both core contraction feedback 116 and qualifying movement feedback 119 may be utilized in Use. No. 3. Use No. 4 is untethered mode, another Out-of-Session 109 use model, that may provide constant reminding to the user 101 to contract their core during qualifying movements performed throughout the day. Use No. 4 utilizes qualifying movement feedback. Each of the elements in table 231 are enabled by the inventive system. The elements in table 231 include examples of the way the inventive system may be programmed and used. In different embodiments, additional ways of using the inventive system may be practiced. The elements shown in the table 231 practiced together both with and without a therapist 107, both in-session 108 and out-of-session 109 in its totality may be beneficial for helping users 101 develop procedural memory for core support of qualifying movements and utilize their core muscles more effectively and more regularly.

The figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical functions. It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems which perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Some embodiments of the invention are implemented as a program product for use with an embedded processor. The program(s) of the program product defines functions of the embodiments (including the methods described herein) and can be contained on a variety of signal-bearing media. Illustrative signal-bearing media include, but are not limited to: (i) information permanently stored on non-writable storage media; (ii) alterable information stored on writable storage media; and (iii) information conveyed to a computer by a communications medium, such as through a computer or telephone network, including wireless communications. The latter embodiment specifically includes information downloaded from the Internet and other networks. Such signal-bearing media, when carrying computer-readable instructions that direct the functions of the present invention, represent embodiments of the present invention.

In general, the routines executed to implement the embodiments of the invention, may be part of an operating system or a specific application, component, program, module, object, or sequence of instructions. The computer program of the present invention typically is comprised of a multitude of instructions that will be translated by the native computer into a machine-accessible format and hence executable instructions. Also, programs are comprised of variables and data structures that either reside locally to the program or are found in memory or on storage devices. In addition, various programs described hereinafter may be identified based upon the application for which they are implemented in a specific embodiment of the invention. However, it should be appreciated that any particular program nomenclature that follows is used merely for convenience, and thus the invention should not be limited to use solely in any specific application identified and/or implied by such nomenclature.

The present invention and some of its advantages have been described in detail for some embodiments. It should be understood that although the process is described with reference to a device, system, and method for developing core contraction procedural memory, the process may be used in other contexts as well. It should also be understood that various changes, substitutions and alterations can be made herein without departing from the spirit and scope of the invention as defined by the appended claims. An embodiment of the invention may achieve multiple objectives, but not every embodiment falling within the scope of the attached claims will achieve every objective. Moreover, the scope of the present application is not intended to be limited to the particular embodiments of the process, machine, manufacture, composition of matter, means, methods and steps described in the specification. A person having ordinary skill in the art will readily appreciate from the disclosure of the present invention that processes, machines, manufacture, compositions of matter, means, methods, or steps, presently existing or later to be developed are equivalent to, and fall within the scope of, what is claimed. Accordingly, the appended claims are intended to include within their scope such processes, machines, manufacture, compositions of matter, means, methods, or steps.

What is claimed is:

1. A method for detecting core muscle usage, comprising:
providing a contraction sensor in communication with a signal processor, the contraction sensor having a bumper core sensor interface extending from the contraction sensor;
placing the bumper core sensor interface of the contraction sensor against core muscles of a user;
attaching an extender cap to the bumper core sensor interface extending from the contraction sensor to extend an effective height or an effective girth of the bumper core sensor interface;
detecting a parameter related to a contraction status of the core muscles with the bumper core sensor interface of the contraction sensor wherein the contraction sensor emits an electrical signal;
converting the electrical signal into a digital value by the signal processor; and
determining by the signal processor the contraction status of the core muscles is either contracted when the digital value is greater than a threshold value or relaxed when the digital value is less than the threshold value.

2. The method of claim 1 further comprising:
emitting a core contraction status signal by an output device coupled to the signal processor indicating the contraction status of the core muscles when the digital value is greater than the threshold value.

3. The method of claim 1 further comprising:
receiving the core contraction status signal by a receiver coupled to a smart device; and
displaying a core contraction status on a visual display coupled to the signal processor.

4. The method of claim 3 further comprising:
monitoring the smart device by a therapist.

5. The method of claim 1 further comprising:
providing a cavity in the bumper core sensor interface with a force sensor or a pressure sensor at a bottom of the cavity and a rubber bumper with a brim over the force sensor or the pressure sensor wherein the rubber bumper interfaces to the force sensor or the pressure sensor and the core muscles of the user; and
placing a frame over the brim of the rubber bumper to hold the rubber bumper in place, and connecting the frame to the contraction sensor.

6. A method for detecting core muscle usage, comprising:
providing a contraction sensor in communication with a transmitter and a smart device, the contraction sensor having a bumper core sensor interface extending from the contraction sensor;
placing the bumper core sensor interface of the contraction sensor against core muscles of a user;
attaching an extender cap to the bumper core sensor interface extending from the contraction sensor to extend an effective height or an effective girth of the bumper core sensor interface;
detecting a parameter related to a contraction status of the core muscles with the bumper core sensor interface of the contraction sensor;
generating core contraction signals based upon the parameter detected by the contraction sensor wherein the core contraction signals are electrical signals;
converting the electrical signals into digital core contraction signals;
transmitting the digital core contraction signals from the transmitter to the smart device; and
determining by the smart device that the contraction status of the core muscles is either contracted when the digital core contraction signals are greater than a threshold value or relaxed when the digital core contraction signals are less than a threshold value.

7. A method of claim 6 further comprising:
emitting a core status signal by the smart device indicating the contraction status of the core muscles.

8. The method of claim 6 further comprising:
detecting by the smart device, a timing relationship between a user movement and a core contraction;
determining by the smart device, that the user movement is either: a protected qualifying movement where the user movement is a qualifying movement that benefits from the core contraction and the digital core contraction signals are greater than the threshold value during the user movement, or an unprotected movement where the user movement is not the qualifying movement or the digital core contraction signals are lower than the threshold value during the user movement detected;
counting the protected qualifying movements and the unprotected qualifying movements by the smart device;
determining a core score for the user by the smart device based upon the protected qualifying movements and the unprotected qualifying movements; and
displaying the core score from the smart device.

9. The method of claim 6 further comprising:
monitoring the smart device by a therapist.

10. The method of claim 6 further comprising:
storing core sensor calibration procedures in the smart device; and
emitting a core calibration signal by the smart device indicating that a threshold value has been detected by the contraction sensor.

11. The method of claim 6 further comprising:
providing a cavity in the bumper core sensor interface with a force sensor or a pressure sensor at a bottom of the cavity and a rubber bumper with a brim over the force sensor or the pressure sensor wherein the rubber bumper interfaces to the force sensor or the pressure sensor and the core muscles of the user; and
placing a frame over the brim of the rubber bumper to hold the rubber bumper in place, and connecting the frame to the contraction sensor.

* * * * *